United States Patent [19]

Arora et al.

[11] Patent Number: 5,298,494

[45] Date of Patent: Mar. 29, 1994

[54] MONOSACCHARIDES HAVING ANTI-PROLIFERATION AND ANTI-INFLAMMATORY ACTIVITY, COMPOSITIONS AND USES THEREOF

[75] Inventors: Sudershan K. Arora, Lansdale, Pa.; Roy L. Whistler, West Lafayette, Ind.; Albert V. Thomas, Vernon Hills, Ill.

[73] Assignee: Greenwich Pharmaceuticals Incorporated, Fort Washington, Pa.

[21] Appl. No.: 83,879

[22] Filed: Jun. 30, 1993

Related U.S. Application Data

[63] Continuation of Ser. No. 8,012, Nov. 13, 1992, abandoned, which is a continuation of Ser. No. 757,817, Sep. 11, 1991, abandoned, and a continuation-in-part of Ser. No. 581,542, Sep. 12, 1990, abandoned, which is a continuation-in-part of Ser. No. 294,838, Jan. 9, 1989, Pat. No. 4,996,195.

[51] Int. Cl.$^5$ .................. A61K 31/00; A61K 31/70; C07H 15/00
[52] U.S. Cl. ........................ 514/23; 536/1.11; 536/4.1; 536/17.2; 536/17.3; 536/17.5; 536/18.7; 536/54; 514/825; 514/861
[58] Field of Search ............... 514/23, 825, 861; 536/1.11, 4.1, 17.2, 17.3, 17.5, 18.7, 54

[56] References Cited

U.S. PATENT DOCUMENTS

| | | | |
|---|---|---|---|
| Re. 30,354 | 7/1980 | Gordon | 536/4 |
| Re. 30,379 | 8/1980 | Gordon | 536/4 |
| Re. 32,268 | 10/1986 | Gordon | 514/23 |
| 2,461,478 | 2/1949 | Kaszuba | 106/135 |
| 2,715,121 | 8/1955 | Lawrence et al. | 260/209 |
| 2,875,194 | 2/1959 | Baker et al. | 260/211 |
| 2,960,452 | 11/1960 | Slager et al. | 204/78 |
| 3,586,664 | 6/1971 | Kohno et al. | 260/210 R |
| 3,832,355 | 8/1974 | Jaffee et al. | 260/340.7 |
| 3,939,145 | 2/1976 | Gordon | 260/210 R |
| 3,939,146 | 2/1976 | Gordon | 260/210 R |
| 3,940,383 | 2/1976 | Fujiwara et al. | 260/210 R |
| 3,965,262 | 6/1976 | Gordon | 424/180 |
| 3,978,041 | 8/1976 | Jaeggi et al. | 536/4 |
| 4,010,275 | 3/1977 | Wulhelmi | 424/285 |
| 4,016,261 | 4/1977 | Gordon | 424/180 |
| 4,017,608 | 4/1977 | Gordon | 424/180 |
| 4,032,650 | 6/1977 | Mille et al. | 424/278 |
| 4,056,322 | 11/1977 | Gordon et al. | 536/4.1 |
| 4,151,277 | 4/1979 | Albrecht et al. | 424/180 |
| 4,220,782 | 9/1980 | Stoltefuss | 546/242 |
| 4,251,520 | 2/1981 | Bruzzese et al. | 424/180 |
| 4,395,405 | 7/1983 | Noda et al. | 424/180 |
| 4,554,349 | 11/1985 | Ponpipom et al. | 536/55 |
| 4,735,934 | 4/1988 | Gordon | 514/25 |
| 4,738,953 | 4/1988 | Gordon | 514/25 |
| 4,996,195 | 2/1991 | Ronsen et al. | 514/23 |
| 5,010,058 | 4/1991 | Ronsen et al. | 514/23 |

FOREIGN PATENT DOCUMENTS

| | | |
|---|---|---|
| 2370753 | 6/1978 | France . |
| 2457300 | 12/1980 | France . |

OTHER PUBLICATIONS

Reckendorf et al., "Über die 6-Amino-6-desoxy-L-idose," Chem. Ber. vol. 101, 1968, pp. 2294-2301.
Robins, et al., "Nucleic Acid Related Compounds. 30. Transformations of Adenosine To The First 2′,3′-Aziridine-Fused Nucleosides, 9-(2,3-Epimino-2,-3-dideoxy-β-D-ribofuranosyl)adenine and 9-(2,3-Epimino-2,3-dideoxy-β-D-lyxofuranosyl)adenine," J. Org. Chem., vol. 44, No. 8, 1979, pp. 1317-1322.
Boschelli et al., "Synthesis of Amphotericin B. 2. Fragment C-D of the Aglycone," Tetrahedron Letters, vol. 26, No. 43, 1985, pp. 5239-5242.
Chemical Abstracts, vol. 107, No. 9, Aug. 31, 1987, p. 265, abstract no. 72877s.
Chemical Abstracts, vol. 73, No. 3, Jul. 20, 1970, p. 397, abstract no. 15166q.
Chemical Abstract 99:16149K, vol. 99, 1983.
Chemical Abstract 160029e, vol. 78, 1973.
Cortes-Garcis, R. et al., "Acetalation of Sucrose by Acetal Exchange with Concomitant Fission of the Glycosidic Bond. Some New Acetals of D-Glucose and Methyl α-D-Fructofuranose," J. C. S. Perkin I, 1981, p. 3176.
Haraguchi, Y. et al., "A Specific Inhibitor of IgE-Antibody Formation: n-Pentyl β-D-Fructopyranoside," J. Med. Chem. 1982, 25, 1495.
Reitz et al., "Carbohydrate Biguanides as Potential Hypoglycenic Agents," J. Med. Chem. 1989, 32, 2110-2116.
Jary et al., "Synthesis Of 3-Amino- And 6-Amino-Deoxyhexoses Of The gluco And Allo Configuration," Collection Czechoslov. Chem. Commun., 1969, 34 1452-1458.

*Primary Examiner*—Ronald W. Griffin
*Attorney, Agent, or Firm*—Finnegan, Henderson, Farabow, Garrett & Dunner

[57] ABSTRACT

Derivatives of simple monosaccharides which exhibit anti-proliferative and/or anti-inflammatory activity and are useful for treating mammals having inflammatory disorders and/or autoimmune disorders. This invention also encompasses pharmaceutical compositions containing these compounds and methods of treating inflammatory and/or autoimmune disorders.

11 Claims, No Drawings

MONOSACCHARIDES HAVING ANTI-PROLIFERATION AND ANTI-INFLAMMATORY ACTIVITY, COMPOSITIONS AND USES THEREOF

This application is a continuation of application Ser. No. 08/008,012 filed Nov. 13, 1992, now abandoned, which is a continuation of application Ser. No. 07/757,817, filed Sep. 11, 1991, abandoned, and a continuation-in-part of application Ser. No. 07/581,542, filed Sep. 12, 1990, abandoned, which is a continuation in part of application Ser. No. 07/294,838, filed Jan. 9, 1989, now U.S. Pat. No. 4,996,195.

I. FIELD OF THE INVENTION

The compounds of this invention are derivatives of simple monosaccharides which exhibit anti-proliferation and anti-inflammatory activity and are useful for treating mammals having inflammatory disorders and/or autoimmune disorders. This invention also encompasses pharmaceutical compositions containing these compounds and methods of treating inflammatory and/or autoimmune disorders.

II. DESCRIPTION OF THE RELATED ART

Certain monosaccharides and their derivatives are known to have therapeutic value in the treatment of inflammatory and autoimmune disorders. Derivatization of monosaccharides at specific hydroxyl groups may be accomplished by synthetic techniques which are known in the art. For example, it is common to block or protect one or more of the hydroxyl groups leaving one or more hydroxyl groups free to undergo derivatization, such as formation of an ether group. Various blocking groups and methods are described, for example, in U.S. Pat. Nos. 2,715,121 and 4,056,322, the disclosures of which are incorporated herein by reference.

Various derivatives of five and six carbon monosaccharides, as well as synthetic methods, are described, for example, in U.S. Pat. Nos. Re. 30,354, Re. 30,379, Re. 32,268, 4,056,322, 4,735,934, 4,738,953, 4,996,195 and 5,010,054. The therapeutic activity of the various substituted monosaccharides is also disclosed in the above documents. The disclosures of these patents are also incorporated herein by reference.

A known derivative of a-D-glucose having beneficial therapeutic properties is amiprilose, 1,2-O-isopropylidene 3-O-3'-(N,N'-dimethylamino-n-propyl)-α-D-glucofuranose, and its hydrochloric acid salt, amprilose HCl (THERAFECTIN ®). These two compounds are known to have anti-inflammatory activity and demonstrated utility in managing the signs and symptoms of rheumatoid arthritis. More generally, these compounds have immunomodulatory activity, and therefore have a therapeutic effect on other autoimmune disorders such as psoriasis, eczema or systemic lupus erythematosus.

Unfortunately, though some derivatives of the monosaccharides have shown beneficial therapeutic activity, high doses of these derivatives, such as THERAFECTIN ®, are often needed to produce effective results. Because therapy for inflammatory or autoimmune disorders is often mid-term or long-term, there is a need to develop more potent, non-toxic compounds which can be orally administered, and thereby promote patient compliance. This invention describes additional monosaccharide derivatives with increased potency.

It is therefore an object of the present invention to provide new compounds and compositions which exhibit anti-proliferation and anti-inflammatory activity.

It is also an object of the invention to provide compounds and compositions which are useful in the treatment of mammals having inflammatory and/or autoimmune disorders.

It is a further object to provide new compounds that exhibit significantly increased potency over available compounds, such as THERAFECTIN ®, in order to provide ease of oral administration.

II. Summary of the Invention

To achieve the foregoing objects and in accordance with the purposes of the invention as embodied and broadly described herein, there is provided monosaccharides, having the following formulae:

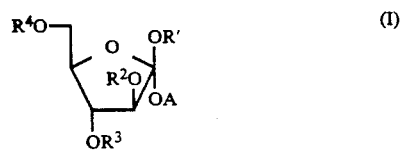
(I)

wherein A is H, methyl or ethyl;
$R^1$ and $R^2$ are H, methyl, $C_5$-$C_{10}$ alkenyl or together form an isopropylidene ring;
$R^3$ is H, $C_5$-$C_{10}$ alkyl, $C_5$-$C_{10}$ alkenyl, $C_5$-$C_{10}$ alkynyl, benzyl, or $C_5$-$C_{10}$ ester; and
$R^4$ is H, $C_5$-$C_{10}$ alkyl, $C_5$-$C_{10}$ alkenyl, $C_5$-$C_{10}$ alkynyl, benzyl, or $C_5$-$C_{10}$ ester;

A compound of formula II

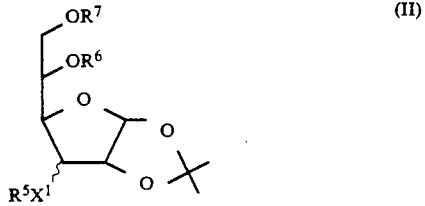
(II)

wherein:
$X^1$ is O and
$R^5$ is $C_{12}$-$C_{20}$ alkyl, or $C_nH_{2n}Y$, wherein n=1,2,3 or 4 and Y is selected from cyano, pyrrolyl, pyrrolidinyl, methylpyrrolidinyl, pipecolinyl, imidazolyl, pyrazolyl, pyrazolinyl, pyrazolidinyl, oxazolyl, oxazolidinyl, isooxazolyl, isooxazolidinyl, imidazolidinyl, piperidinyl, piperazinyl, morpholinyl, $O(CH_2)_3N(CH_3)_2$($C_5$-$C_{10}$ alkoxy), $CH_2CH(CH_3)CH_2N(CH_3)_2$, $CH_2CH_2N(C_5$-$C_{10}$ alkyl )$_2$, or ($C_3$-$C_7$ alkenyl), or
$X^1$ is NH and
$R^5$ is $C_2$-$C_{10}$ alkyl, or
$C_nH_{2n}Y$ wherein n=1,2,3 or 4 and Y is selected from hydroxy, cyano, pyrrolyl, pyrrolidinyl methylpyrrolidinyl, pipecolinyl, imidazolyl, pyrazolyl, pyrazolinyl, pyrazolidinyl, oxazolyl, oxazolidinyl, isoxazolyl, isooxazolidinyl, imidazolidinyl, piperidinyl, piperazinyl, morpholinyl, $O(CH_2)_3N(CH_3)_2$, ($C_5$-$C_{10}$ alkoxy), or phenyl; and
$R^6$ and $R^7$ are hydrogen or form an isopropylidene ring; A compound of formula III:

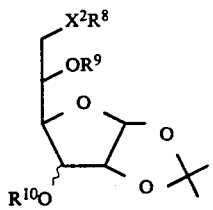

(III)

wherein X² is O,

R⁸ is C₈–C₂₀ alkyl, or $C_nH_{2n}Y$, wherein n=1,2,3, or 4 and

Y is selected from phenyl, cyano, pyrrolyl, methylpyrrolidinyl, pipecolinyl, imidazolyl, pyrazolyl, pyrazolinyl, pyrazolidinyl, oxazolyl, oxazolidinyl, isooxazolyl, isooxazolidinyl, imidazolidinyl, piperidinyl, piperazinyl, morpholinyl, $O(CH_2)_3N(CH_3)_2$, (C₅–C₁₀ alkoxy), NH or $N(CH_3)_2$; or X² is NH and R⁸ is H, or $C_nH_{2n}Y$, wherein n=1,2,3 or 4 and Y is selected from OH, cyano, pyrrolyl, pyrrolidinyl, methylpyrrolidinyl, pipecolinyl, imidazolyl, pyrazolyl, pyrazolinyl, pyrazolidinyl, oxazolyl, oxazolidinyl, isooxazolyl, isoozazolidinyl, imidazolidinyl, piperidinyl, piperazinyl, morpholinyl, $O(CH_2)_3N(CH_3)_2$ or (C₅–C₁₀ alkoxy) or phenyl; or X² is S and R⁸ is C₅–C₁₀ alkyl, or $C_nH_{2n}Y$ wherein n=1,2,3 or 4 and Y is selected from OH, phenyl, cyano, pyrrolyl, pyrrolidinyl, methylpyrrolidinyl, pipecolinyl, imidazolyl, pyrazolyl, pyrazolinyl, pyrazolidinyl, oxazolyl, oxazolidinyl, isooxazolyl, isoozazolidinyl, imidazolidinyl, piperidinyl, piperazinyl, morpholinyl, $O(CH_2)_3N(CH_3)_2$ or (C₅–C₁₀ alkoxy); and R⁹ and R¹⁰ are hydrogen or form an isopropylidene group; and A compound selected from (3S) 1,2-O-isopropylidene-α-D-ribo-hexos-3-ulose-1,4:3,6-difuranose; and Methyl 3-O-3'-(N',N'-dimethylamino-n-propyl)-6-deoxy-D-glucopyranoside.

Other embodiments in accordance with the present invention are pharmaceutical compositions containing an effective amount of one or more of the above compounds, and a method of treating an inflammatory disorder and/or an autoimmune disorder comprising administering an effective amount of a compound described above.

IV. Detailed Description of the Preferred Embodiments

Monosaccharides are known to exist in an equilibrium between hemiacetal cyclic structures and an open chain sugar. The preferred cyclic structures are furanoses (5-membered ring structures) and pyranoses (6-membered ring structures). other ring structures may be formed but are not as thermodynamically stable and generally rearrange to form the pyranose or furanose structures. When a cyclic hemiacetal is reacted with an alcohol, an acetal is formed.

A glycoside can be defined as a cyclized derivative of a monosaccharide having two ether (O-R groups) substituents on the acetal carbon of the sugar. One of these ether substituents is the carbocylic ring. The second ether substituent is formed by the reaction with the alcohol and is termed the aglycon. Because of the second ether substituent, the resultant glycoside is stable and does not exist in an equilibrium with its open chain structure. Glycosides having a 5-membered ring are known as furanosides, those with 6-membered ring as pyranosides.

One embodiment of the present invention relates to derivatives of the simple monosaccharide fructose, in particular to fructofuranosides. Fructofuranosides can be in an α-D or β-D configuration. The fructofuranosides of the present invention, shown below in formula I, encompass both α or β configurations and are substituted at one or more of the free hydroxyl groups, but, preferably, have at least one free hydroxyl group. As discussed above, the techniques to form these derivatives of the present invention are generally known in carbohydrate chemistry.

The fructofuranosides of the present invention are represented by formula (I):

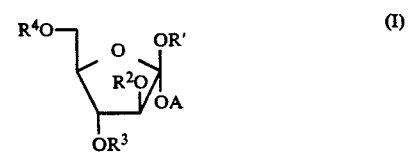

(I)

wherein the aglycon, A, is methyl or ethyl, preferably methyl;

R¹ and R² are H, methyl, ethyl, C₅–C₁₀ alkenyl or together form an isopropylidene ring;

R³ is H, C₅–C₁₀ alkyl, C₅–C₁₀ alkenyl, C₅–C₁₀ alkynyl, 2-octyne, benzyl, or C₅–C₁₀ ester; and R⁴ is H, C₅–C₁₀ alkyl, C₅–C₁₀ alkenyl, C₅–C₁₀ alkynyl, 2-octyne, benzyl, or C₅–C₁₀ ester.

Preferred fructofuranosides of formula I where A is methyl are shown in Table I.

TABLE I

| Compound | R¹ | R² | R³ | R⁴ |
|---|---|---|---|---|
| (Ia) | R¹ & R² = isopropylidene | | H | C₇H₁₅ |
| (Ib) | C₂H₅ | C₂H₅ | H | C₇H₁₅ |
| (Ic) | R¹ & R² = isopropylidene | | C₇H₁₅ | H |
| (Id) | R¹ & R² = isopropylidene | | 2-octynyl | 2-octynyl |
| (Ie) | R¹ & R² = isopropylidene | | trans-2-octenyl | trans-2-octenyl |
| (If) | R¹ & R² = isopropylidene | | cis-2-octenyl | cis-2-octenyl |
| (Ig) | cis-2-octene | H | H | cis-2-octenyl |
| (Ih) | R¹ & R² = isopropylidene | | CC₇H₁₅O | H |
| (Ii) | R¹ & R² = isopropylidene | | H | CC₇H₁₅O |
| (Ij) | R¹ & R² = isopropylidene | | CC₇H₁₅O | CC₇H₁₅O |

The compounds included in Table I are:

methyl 1,3-O-isopropylidene-6-O-heptyl-α-D-fructofuranoside (Ia);

methyl 1,3-di-O-ethyl-6-O-heptyl-α-D-fructofuranoside (Ib);

methyl 1,3-O-isopropylidene-4-O-heptyl-α-D-fructofuranoside (Ic);

methyl 1,3-O-isopropylidene-4,6-di-O-(2-octynyl)-α-D-fructofuranoside (Id);

methyl 1,3-O-isopropylidene-4,6-di-O-(trans,2-octenyl)-α-D-fructofuranoside (Ie);

methyl 1,3-O-isopropylidene-4,6-di-O-(cis,2-octenyl)-α-D-fructofuranoside (If);

methyl 1,6-di-O-(cis,2-octenyl)-α-D-fructofuranoside methyl 1,3-O-isopropylidene-4-O-octanoyl-α-D-fructofuranoside (Ih);

methyl 1,3-O-isopropylidene-6-O-octanoyl-α-D-fructofuranoside (Ii); and methyl 1,3-O-isopropylidene-4,6-di-O-octanoyl-α-D-fructofuranoside (IJ).

The present invention also relates to fructofuranoses. These compounds have the same substituents as defined in formula I where A is hydrogen. A particularly preferred compound is: 2,3-O-isopropylidene-4-O-heptyl-β-D-fructofuranose (Ik).

The following Examples 1–4 illustrate the preparation of representative compounds of formula I according to this invention. The activity of these compounds is illustrated in Example 5.

EXAMPLE 1

Preparation of methyl 1,3-O-isopropylidene-6-O-n-heptyl-α-D-fructofuranoside, (Ia).

Step 1: The preparation of Methyl α-D-fructofuranoside.

This compound was prepared by the method taught by Cortez-Garcia, R., L. Hough, and A. C. Richardson (Journal of the Chemical Society, Perkin 1, pp. 3176–3181, 1981) except that a silica gel column was used, eluted with chloroform-methanol (9:1 to 8:2) to give: methyl β-D-fructofuranoside 23.8%; $[\alpha]_D^{25}$ +81.60 (c 1.02, ethanol). {Cortez-Garcia, 22.5% $[\alpha]_D^{25}$ +90° (c 2, water)} methyl β-D-fructofuranoside 28.2%; $[\alpha]_D^{25}$ −47.8° (c 1.23, ethanol). {Cortez-Garcia, 35%; $[\alpha]_D^{25}$ −49° (c 2, methanol)}.

Step 2: The preparation of Methyl 1,3-O-isopropylidene-α-D-fructofuranoside.

Method one: The reaction procedure was described by Cortez-Garcia, except the longer reaction time was used (three days). The best yield was 50%. $[\alpha]_D^{25}$ +40.1° (c 1.79, chloroform). {Cortez-Garcia 33%, $[\alpha]_D$ +42.5° (methanol)}. The compound had physical properties in agreement with literature values.

Method two: A mixture of methyl α-D-fructofuranoside (0.8 g, 4.1 mmole), dimethoxypropane (5 g, 49 mmole, 6 ml) and p-toluenesulfonic acid (0.1 g, 0.5 mmole) in 20 ml of DMF was stirred at 25° C. for 24 hours. Sodium bicarbonate was added to neutralize the solution. The solvent was filtered and the filtrate was evaporated to dryness. Column chromatography {petroleum ether-ethyl acetate (8:2 to 7:3) then chloroform-methanol (9:1)} gave methyl 1,3-O-isopropylidene-α-D-fructofuranoside (0.38 g, 39%).

Step 3: The preparation of Methyl 1,3-O-isopropylidene-6-O-pivaloyl-α-D-fructofuranoside.

Methyl 1,3-O-isopropylidene-α-D-fructofuranoside (1.3 g, 5.55 mmole) was dissolved in methylene chloride (10 ml) and pyridine (7 ml). To this solution, pivaloyl chloride (0.68 g, 5.68 mmole, 0.7 ml) was added at 2° C. The solution was stirred and the temperature rose to 25° C. After 18 hours, another 0.1 ml of pivaloyl chloride (0.8 mmole) was added and stirring was continued for 24 hours. Water was added to the mixture and solvent was evaporated. The residue was extracted with chloroform, washed with water, brine, dried over sodium sulfate, and concentrated. Column chromatography {petroleum ether-ethyl acetate (9:1 to 7:3)} gave methyl 1,3-O-isopropylidene-6-O-pivaloyl-α-D-fructofuranoside (1.3 g, 83%). $[\alpha]_D^{25}$ +30.9° (c 2.34, methylene chloride). $^1$H-N.m.r. (CDCl$_3$): δ4.4–3.9 (m, 8H), 3.3 (s, 3H, OCH$_3$), 1.45, 1.38 (2 s, each 3H, C(CH$_3$)$_2$), 1.23 (s, 9H, CO(CH$_3$)$_3$) PPM.

Step 4: The preparation of Methyl 1,3-O-isopropylidene-4-O-benzyl-6-O-pivaloyl-α-D-fructofuranoside.

Methyl 1,3-O-isopropylidene-6-O-pivaloyl-α-D-fructofuranoside (1.3 g, 4.08 mmole) was dissolved in DMF (15 ml) and 5.2 ml of benzylbromide (7.4 g, 43.7 mmole) was added. To this solution, a total 5.2 g of silver (I) oxide (22.4 mmole) was added in three portions during one hour with stirring. Stirring was continued at 25° C. for two days. The silver salt was filtered and washed with DMF and methylene chloride, and solvent was removed under reduced pressure. The residue was extracted with methylene chloride and the extract was washed with water, brine, dried and concentrated. Column chromatography {petroleum ether-ethyl acetate (50:1)} gave methyl 1,3-O-isopropylidene-4-O-benzyl-6-O-pivaloyl-α-D-fructofuranoside $[\alpha]_D^{25}$ +50.7° (c 1.35, chloroform). $^1$H-N.m.r. (CDCl$_3$): δ7.33 (m, 5H, C$_6$H$_5$), 4.60 (dd, 2H, OCH$_2$Ph), 4.3–4.1 (m, 4H), 3.9 (d, 1H, J 12.1 Hz, H-1), 3.8 (m,1H), 3.7 (d,, 1H, J 12.1 Hz, H-1), 3.3 (8, 3H, OCH$_3$), 1.4–1.3 (2 s, each 3H, C(CH$_3$)$_2$), 1.2 (s, 9H, CO(CH$_3$)$_3$) PPM.

Step 5: The preparation of Methyl 1,3-O-isopropylidene-6-O-t-butyldimethylsilyl-α-D-fructofuranoside.

To a solution of methyl 1,3-O-isopropylidene-α-D-fructofuranoside (0.25 g, 1.07 mmole) in DMF (5 ml) was added imidazole (0.16 g, 2.3 mmole) and t-butyldimethylsilyl chloride (0.2 g 1.32 mmole). The mixture was stirred at 25° C. for 48 hours. Water was added and solvent was evaporated under reduced pressure. Column chromatography (petroleum ether-ethyl acetate (9:1 to 8:2)) gave methyl 1,3-O-isopropylidene-6-O-t-butyldimethylsilyl-α-D-fructofuranoside (0.26 g, 97%), then using chloroform-methanol (100:1) gave starting material methyl 1,3-O-isopropylidene-α-D-fructofuranoside (70 mg). Methyl 1,3-O-isopropylidene-6-O-t-butyldimethylsilyl-α-D-fructofuranoside: $[\alpha]_D^{25}$ +21.3° (c 1.01, chloroform). $^1$H-N.m.r. (CDCl$_3$): δ4.1–3.7 (m, 7H), 3.3 (s, 3H, OCH$_3$), 2.6 (d, 1H, OH), 1.45–1.35 (2 s, each 3H, C(CH$_3$)$_2$), 0.9 (s, 9H, t-Bu), 0.1 (s, 6H, Si(CH$_3$)$_2$) ppm.

Step 6: The preparation of Methyl 1,3-O-isopropylidene-4-O-benzyl-6-O-t-butyldmethylsilyl-α-D-fructofuranoside.

To a solution of methyl 1,3-O-isopropylidene-6-O-t-butyldimethylsilyl-α-D-fructofuranoside (0.26 g, 0.75 mmole) and benzyl bromide (0.15 g, 0.9 mmole, 0.1 ml) in DMF (2 ml) was added 80% sodium hydride (25 mg, 0.83 mmole) slowly. The mixture was stirred at 25° C. under nitrogen for 40 minutes. Methanol was added to destroy the excess sodium hydride and solvent was removed under reduced pressure at 25° C. The residue was extracted with chloroform, washed with water, brine, dried and concentrated. Column chromatography {(petroleum ether-ethyl acetate (20:1 to 8:2)} gave methyl 1,3-O-isopropylidene-4-O-benzyl-6-O-t-butyldimethylsilyl-α-D-fructofuranoside (0.28 g) 85.6%) and methyl 1,3-O-isopropylidene-4-O-benzyl-α-D-fructofuranoside (10 mg, 4%). Methyl 1,3-O-isopropylidene-4-O-benzyl-6-O-t-butyldimethylsilyl-α-D-fructofuranoside: $[\alpha]_D^{25}$ +48.70 (c 1.58, chloroform). $^1$H-N.m.r. (CDCl$_{13}$): δ7.3 (m, 5H, C$_6$H$_5$), 4.6 (s, 2H, OCH$_2$Ph), 4.1–3.7 (m,7H), 3.3 (s, 3H, OCH$_3$), 1.4–1.3 (2 s, each 3H, C(CH$_3$)$_2$), 0.9 (9, 9H, t-Bu), 0.06 (s, 6H, Si(CH$_3$)$_2$) ppm.

Step 7: The preparation of Methyl 1,3-O-isopropylidene-4-O-benzyl-α-D-fructofuranoside.

Method one: Methyl 1,3-O-isopropylidene-4-O-benzyl-6-O-pivaloyl-α-D-fructofuranoside was dissolved in methanol (20 ml) and sodium methylate (0.2 g) was added and stirred at 25° C. for 20 hours. The reaction solution was neutralized with Amberlite IR-120 (H+) ion exchange resin, filtered and concentrated. Column chromatography {petroleum ether-ethyl acetate (9:1 to 8:2)} gave methyl 1,3-O-isopropylidene-4-O-benzyl-α-D-fructofuranoside (1.15 g, 86.8% yield).

Method two: A solution of methyl 1,3-O-isopropylidene-4-O-benzyl-6-O-t-butyldimethylsilyl-α-D-fructofuranoside (0.2 g, 0.45 mmole) and 1M t-Bu$_4$NF-THF (0.5 ml, 0.5 mmole) in THF (5 ml) was stirred at 25° C. for 18 hours. Solvent was removed and the residue was chromatographed (petroleum ether-ethyl acetate (8:2)) to give methyl 1,3-O-isopropylidene-4-O-benzyl-α-D-fructofuranoside (0.14 g, 95%).

Method three: To a solution of methyl 1,3-O-isopropylidene-6-O-pivaloyl-α-D-fructofuranoside (0.2 g, 0.63 mmole) and benzyl bromide (0.14 g, 0.81 mmole, 0.1 ml) in DMF (2 ml) was added 80% sodium hydride (27 mg. 0.9 mmole) slowly. The mixture was stirred at 25° C. under nitrogen for 15 minutes. Methanol was added to destroy the excess sodium hydride and solvent was evaporated under reduced pressure at 25° C. The residue was dissolved in methanol (5 ml) and sodium methylate (0.1 g) was added. The mixture was stirred at 25° C. for 10 hours and neutralized with Amberlite ∫R-120 (H+) resin, filtered and concentrated. Column chromatography {petroleum ether-ethyl acetate (9:1 to 8:2)} gave methyl 1,3-O-isopropylidene-4-O-benzyl-α-D-fructofuranoside (0.13 g, 64%). $[\alpha]_D^{25}$ +83.70 (c 0.98, methylene chloride). $^1$H-N.m.r. (CDCl$_3$): δ7.3 (m, 5H, C$_6$H$_5$), 4.6 (dd, 2H, OCH$_2$Ph), 4.1 (m, 2H), 3.9–3.8 (m, 4H), 3.6 (dd, 1H), 3.3 (s, 3H, OCH$_3$), 2.1 (s, 1H, OH), 1.4–1.3 (2s, each 3H, C(CH$_3$)$_2$) ppm.

Step 8: The preparation of Methyl 1,3-O-isopropylidene-4-O-benzyl-6-O-n-heptyl-α-D-fructofuranoside.

To a solution of methyl 1,3-O-isopropylidene-4-O-benzyl-α-D-fructofuranoside (1.63 g, 5.03 mmole) and bromoheptane (4.1 g, 23 mmole, 3.6 ml) in DMF (35 ml) was added 80% sodium hydride (0.6 g, 20 mmole) slowly. The mixture was stirred at 25° C. for 1.5 hours. Methanol was added to destroy the excess sodium hydride and solvent was evaporated. The residue was extracted with chloroform, washed with water, brine, dried over anhydrous sodium sulfate and concentrated. Column chromatography {petroleum ether-ethyl acetate (9:1)} gave methyl 1,3-O-isopropylidene-4-O-benzyl-6-O-n-heptyl-α-D-fructofuranoside (2 g, 94%). $[\alpha]_D^{25}$ +51.9° (c 1.29, methylene chloride). $^1$H-N.m.r. (CDCl$_3$): δ7.3 (m 5H, C$_6$H$_5$), 4.6 (q, 2H, OCH$_2$Ph), 4.1 (m, 2H), 3.9 (d, 1H), 3.8 (d, 1H), 3.6–3.4 (m, 4H), 3.3 (s, 3H, OCH$_3$), 1.6 9m, 2H, OCH$_2$CH$_2$C$_5$H$_{11}$), 1.4–1.3 (2 s, each 3H, C(CH$_3$)$_2$), 1.2 (br, 8H), 0.9 (t, 3H, CH$_3$) ppm.

Step 9: The preparation of Methyl 1,3-O-isopropylidene-6-O-n-heptyl-α-D-fructofuranoside.

Method one: A mixture of methyl 1,3-O-isopropylidene-4-O-benzyl-6-O-n-heptyl-α-D-fructofuranoside (0.13 g, 0.3 mmole), 10% palladium on activated carbon (26 mg) in methanol (5 ml) was shaken under hydrogen (25 lbs. per sq. inch) for 8 hours. Catalyst was filtered and solvent was removed. Column chromatography {petroleum ether-ethyl acetate (9:1)} gave methyl 1,3-O-isopropylidene-6-O-n-heptyl-α-D-fructofuranoside (Ia) (70 mg, 70%).

Method two: A mixture of methyl 1,3-O-isopropylidene-4-O-benzyl-6-O-n-heptyl-α-D-fructofuranoside (0.22 g, 0.52 mmole), 10% palladium on activated carbon (0.2 g, 400 mg/mmole per Bn) and ammonium formate (0.3 g) in methanol (10 ml) was refluxed for 2 hours. Another 0.25 g of ammonium formate was added and refluxed for 3 hours. A final part of 0.2 g of ammonium formate was added and refluxing was continued for another 2.5 hours. After cooling, catalyst was filtered and washed with methanol, filtrate was evaporated to dryness. Column chromatography {petroleum ether-ethyl acetate (9:1)} gave methyl 1,3-O-isopropylidene-6-O-n-heptyl-α-D fructofuranoside (Ia) (0.14 g, 81% ), $[\alpha]_D^{25}$ +27.40 (c 1.01, methylene chloride). $^1$H-N.m.r. (CDCl$_3$): δ4.2–3.9 (m, 5H), 3.4–3.7 (m, 4H), 3.3 (s, 3H, OCH$_3$), 2.7 (d, 1H), 1.6 (m, 2H), 1.5–1.4 (2 s, each 3H, C(CH$_3$)$_2$), 1.3 (br S, 8H), 0.9 (t, 3H, CH$_3$) ppm. $^{13}$C-NMR (CDCl$_3$): δ102.0 (C-2), 98.6 (C(CH$_3$)$_2$), 85.9, 79.7, 78.7 (C-3, C-4, C-5), 71.7, 71.5 (C-6, O—CH$_2$—C$_6$H$_{13}$), 61.7 (C-1), 48.7 (OCH$_3$), 31.8, 29.5, 29.1, 27.6, 25.9, 22.6, 19.7 14.1 ppm. m.s.: m/z 333 (M+H), 301 (M+H-CH$_3$O—), 260 (M-CH$_2$OC(CH$_3$)$_2$).

Example 2

Preparation of methyl 1,3-O-isopropylidene-4,6-di-O-(2-octynyl)-α-D-fructofuranoside, (Id)

Methyl 1,3-O-isopropylidene-α-D-fructofuranoside was prepared by the procedure of Cortez-Garcia et al. as described in Example 1. To a solution of methyl 1,3-O-isopropylidene-α-D-fructofuranoside (0.3 g, 1.28 mmole) and 1-bromo,2-octyne (0.73 g, 3.85 mmole) in DMF (4 mL) was added 80% NaH (0.12 g, 4.0 mmole) slowly and the mixture was stirred at 25° under nitrogen for 40 min. Methanol was added to destroy the excess sodium hydride and solvent was removed. The residue was extracted with methylene chloride and this solution washed with water, brine and sodium bicarbonate. This solution was then dried with anhydrous sodium sulfate, filtered and evaporated to a residue. This residue was dissolved in eluant and chromatagraphed on a silicagel column using petroleum ether-acetone (24:1) which gave methyl 1,3-O-isopropylidene-4,6-di-O-(2-octynyl)-α-D-fructofuranoside (Id) (0.41 g, 71%) as a colorless oil. The compound was treated with sodium bicarbonate and kept in freezer. The compound was identified by its specific rotation, NmR and mass spectral analysis.

Example 3

Preparation of methyl 113-O-isopropylidene-4,6-di-O-(trans,2-octenyl)-α-D-fructofuranoside, (Ie)

The procedure of Example 2 was followed except that 1-bromotrans-2-octene was substituted for 1-bromo-2-octyne. Methyl 1,3-O-isopropylidene-4,6-di-O-(trans,2-octenyl)-α-D-fructofuranoside was obtained in 70.0% yield as a colorless oil and identified by its specific rotation, NMR and mass spectral analysis.

Example 4

Preparation of 2,3-O-isopropylidene-4-O-heptyl-β,D-fructofuranose (Ik);

Step 1: Preparation of 1,6-Di-O-trityl-D-fructose.

To a solution of D-fructose (10 g, 55.5 mmole) in pyridine (40 ML) and chloroform (25 mL) was added trityl-chloride (35 g, 126.3 mmole) and the mixture was stirred at 25° for 2 days, another 5 g of trityl chloride was added and stirring was continued for 2 days. Solvent was removed under reduced pressure and the residue was extracted with chloroform, washed with aqueous saturated cupric sulfate solution, brine, dried over anhydrous sodium sulfate and concentrated. Column chromatography [chlorofm-methanol (100:1)] gave 1,6-Di-O-trityl-D-fructose (11 g, 30%). This compound was identified by its specific rotation and by NMR and Mass spectrometry.

Step 2: Preparation of 1,6-Di-O-trityl-2,3-O-isopropylidene-β-D-fructosfuranose.

A mixture of 1,6-Di-O-trityl-D-fructose (2 g, 3 mmole), dimethoxypropane (5 mL) and p-toluenesulfonic acid (0.1 g) in DMF (20 mL) was stirred at 25° for 3 h. sodium bicarbonate was added to neutralize the solution. After removal of the salt and solvent, the residue was extracted with chloroform, washed with water and brine, dried and concentrated. Column chromatography [petroleum ether-ethyl acetate] gave 1,6-Di-O-trityl-2,3-O-isopropylidene-β-D-fructosfuranose (0.9 g, 42%). This compound was identified by its specific rotation and by NMR and Mass spectrometry.

Step 3: Preparation of 2,3-O-Isopropylidene-4-O-heptyl-1,6-di-O-trityl-β-D-fructofuranose.

1,6-Di-O-trityl-2,3-O-isopropylidene-β-D-fructosfuranose (0.5 g, 0.71 mmole) was dissolved in DMF (10 mL) and sodium hydride (60%, 0.12 g) was added. The mixture was stirred at 25° C. for 20 min. then 1-bromoheptane (0.62 g, 3.5 mmole) was added and stirred for 1 h. Methanol was added to destroy the excess sodium hydride and solvent was evaporated. The residue was extracted with chloroform, washed with water, brine, dried over anhydrous sodium sulfate and concentrated. Column chromatography [petroleum ether-ethyl acetate (100:1)] gave 2,3-O-Isopropylidene-4-O-heptyl-1,6-di-O-trityl-β-D-fructofuranose, (0.47 g, 82.5%). This compound was identified by its specific rotation and by NMR and Mass spectrometry.

Step 4; Preparation of 2,3-O-Isopropylidene-4-O-heptyl-β-D-fructofuranose.

Ammonia (about 100 ml) was passed through a potassium hydroxide tower and cooled into liquid with dry ice to a solution of 2,3-O-Isopropylidene-4-O-heptyl-1,6-di-O-trityl-β-D-fructofuranose (1.35 g, 1.68 mmole) in dry THF (30 ml) cooled with dry ice. The solution was stirred and pieces of lithium was added until the blue color persisted. The solution was stirred until the reaction was finished (checked with TLC). Ethanol was added to discharge the reaction and ammonia was allowed to evaporate overnight. The residue, chloroform was added and salt was removed. Column chromatography [petroleum ether-acetone (8:2)] gave 2,3-O-Isopropylidene-4-O-heptyl-β-D-fructofuranose (Ik) (0.45 g, 84.1%). This compound was identified by its specific rotation and by NMR and Mass spectrometry.

Example 5

Pharmacological Activity of compounds of Formula I

The pharmacologic assays performed to determine the immunomodulatory effects of the experimental compounds in vitro include the Mixed Lymphocyte Reaction (MLR) and the ConA blastogenesis assay. These assays were used to determine the inhibitory effects of the compounds of the invention on T lymphocyte activation and proliferation. Since inflammation at the cellular level is characterized by T lymphocyte recruitment, activation and proliferation, these assays are appropriate to use as screens for novel compounds having therapeutic potential in the treatment of disorders in which inflammatory mechanisms are involved.

The MLR is a classical assay used to measure T cell function by studying the proliferative response of T cells which are activated in vitro by genetically disparate stimulator cells. This is accomplished by co-culturing spleen cells from two different strains of mice. Splenic T cell proliferation occurs as a result of cellular activation signals generated by the ongoing cellular interactions.

Specific Method: MLR ASSAY

Balb/c mice were euthanised by cervical dislocation and their spleens removed. Single cell suspensions of the spleens were prepared in culture medium (hepes buffered RPMI-1640 supplemented with 10% fetal calf serum, 2mM glutamine, 500 units penicillin/ streptomycin, and $4 \times 10^{-5}$ M 2-mercaptoethanol) using a Teflon pestle. The cells were centrifuged at 1500 rpm and the pellets resuspended in ACT (0.15M tris, 0.14M ammonium chloride, pH 7.2) in order to lyse the red blood cells. After a 5 minute incubation in a 37 C. waterbath, the cells were resuspended in culture medium and counted. C57B1/6 spleen cells which were used as stimulator cells, were also prepared by this method. The stimulator cells were treated with 100 ug/ml of mitomycin c for 1 hour at 37 C. (to inhibit stimulatory cell proliferation) and were then washed 5 times in culture medium. The proliferative responses were measured by culturing $2.5 \times 10^5$ responder cells with $5 \times 10^5$ stimulatory cells in 96 well microtiter plates in the presence or absence of various doses of test compounds or vehicle (DMSO). Syngeneic control cultures using mitomycin c treated Balb/c spleen cells as stimulator cells were also run. All cultures were run in triplicate.

Solutions of compounds of the present invention in DMSO were prepared at a stock concentration of 120 Mm. Dilutions were made in culture medium to the following concentrations: 3, 10, 30, 100, and 300 uM. The vehicle (DMSO) was used as a negative control.

After incubation of for 5 days at 37 C. with 5% $CO_2$, the amount of cell proliferation was measured by adding 20 ul of MTT (3-[4,5-dimethylthiazol-2-yl]-2,5diphenyl-tetrazolium bromide) (10 mg/ml in phosphate buffered saline) to each well. Plates were incubated for 4 hours at 37 C., after which 180 ul of 10% sodium dodecyl sulphate in phosphate buffered saline was added. After an overnight incubation, the optical density (OD) of each well was read on a Molecular Devices microplate reader at 570–650 nm. The results were determined by calculating the difference between the means of the allogeneic cultures and the means of the syngenic cultures for each test article concentration. Differences of the test article groups were compared to the control group and the percent change from the control was determined. Test articles which were found to inhibit proliferation are presented as −()% of control with inhibitions greater than −20% of control being considered active.

Mouse Spleen Cell ConA Blastogenesis Assay

It is well known that several plant lectins, when cultured in vitro with lymphocytes, stimulate cellular activation and proliferation. Concanavolin, (ConA) selectively stimulates the blastogenic response of T lymphocytes. Therefore, the ConA blastogenesis assay is useful for screening the immunomodulatory and anti-proliferative activities of experimental compounds.

Specific Method: ConA Assay

Six to 8 week old male C57Bl/6 mice were purchased from Harlan Sprague Dawley (Indianapolis, Ind.).

Spleens were removed and were homogenized to obtain a single cell suspension. Erythrocytes were lysed by hypotonic shock. Upon determination of the viability and concentration of the lymphoid cells, they were adjusted to $4 \times 10^6$ cells/ml in culture medium (RPMI-1640) supplemented with 10% fetal bovine serum; 100 ug/ml streptomycin; 100 U/ml penicillin, 0.2M hepes buffer; $5 \times 10^{-5}$M 2-mercaptoethanol and 2 mM glutamine). seeded into microtiter plate wells at $2 \times 10^5$ cells/0.050 ml/well. To these cultures were added various doses of experimental compounds and ConA at a final concentration of 4 or 1 ug/ml. Control cultures consisted of cells, ConA and culture medium containing the vehicle, DMSO only. In some assays the positive controls cyclosporin A (CSP) and AZT were also run. For the testing of the methyl 1,3-O-isopropylidene-6-O-n-heptyl-α-D-fructofuranoside compound indomethacin and NDGA were used as controls. All cultures were run in triplicate.

Solutions of compounds of the invention in DMSO were prepared and dilutions were made in culture medium. Assay concentrations were either: 1, 2.5, 10, 25, 100, 300 and 750 ug/ml or 0.001, 0.01, 0.1, 1, 2.5, 10, 25 and 100 ug/ml.

Cultures were incubated for 3 days at 37° C. in a humidified atmosphere of 5% of $CO_2$ in air. For the last 18 hours of culture, 1 uCi of $^3$H-thymidine was also incubated in each well. The cells were precipitated by a multi-channel harvester. The amount of $^3$H-thymidine incorporated by the cultures, as a measure of cell proliferation, was measured in a liquid scintillation counter. The amount of radioactive incorporation is proportional to the amount of cellular proliferation in individual wells. The students T test was used to determine the significance of the difference between experimental and control values.

IL-1 Assay

Interleukin 1 (IL-1) is a potent immunomodulatory cytokine that has a broad range of pro-inflammatory activities. IL-1 is known to be produced by activated accessory cells such as macrophages. Accessory cell production of IL-1 results in the activation and proliferation of T and B lymphocytes. Therefore, by inhibiting macrophage activation and production of IL-1, the activation and proliferation of the cellular effectors of inflammation can be modulated. Compounds of the invention were screened for inhibitory activity in a classical IL-1 assay.

Specific Method: IL-1 Assay

Six to 8 week old male C57Bl/6 mice were purchased from Harlan Sprague Dawley. Peritoneal macrophages were elicited by the administration to mice of a single intraperitoneal injection of 0.2 ml of complete Freund's adjuvant. After 48 hours, elicited macrophages were removed from the mice by lavage with the use of Hank's balanced salt solution.

Macrophages were washed and seeded into microtiter wells at a density of $2 \times 10^5$ cells/well in culture medium (as described in the ConA blastogenesis assay). To the macrophage cultures were added various doses of the compounds of the invention and 10 ug/ml of the macrophage activator lipopolysaccharide (to stimulate IL-1 production). Control cultures consisted of macrophages, lipopolysaccharide and culture medium containing various doses of DMSO only. Cultures were incubated for 24 hours at 37° C. in a humidified atmosphere of 5% $CO_2$ in air. Compounds of the invention were prepared in DMSO and diluted to the following concentrations in culture mediums 0.001, 0.01, 1, 2.5, 10, 25 and 100 ug/ml.

The amount of IL-1 produced in the individual wells was determined in a bioassay for IL-1. This involved the removal of thymuses from mice less than 8 weeks of age. Thymocytes were isolated by passing each thymus through a stainless steel mesh screen. Thymocytes were placed in culture at $1.5 \times 10^6$ cells/well in RPMI-1640 medium containing 5% fetal bovine serum and 1 ug/ml PRA in microtiter plates. Triplicate cultures were cultured with dilutions of macrophage supernatants in the same medium at 37° C. in a humidified atmosphere of 5% $CO_2$ in air.

After 48 hours, wells were pulsed with 0.5 uCi of $^3$H-thymidine. After 18 hours cells were harvested and radioactive incorporation (as a measure of cell proliferation) was quantitated in a liquid scintillation counter. The students t test was used to determine the significance of the difference between experimental and control values.

Results of Screening Assays Performed on Representative of Formula I

A summary of the inhibitory effects of compounds (Ib)–(Ij) on T lymphocyte proliferation as measured in the ConA blastogenesis assay is given in Table II. As demonstrated by these data, the fructofuranosides inhibit dose dependent inhibition of ConA stimulated T lymphocyte proliferation with strong inhibition (greater than −50% of control) by these compounds of the present invention at 100 ug/ml with the exception of (Ii) which was found to be a less potent inhibitor of the mitogen induced T lymphocyte proliferative response.

Tables III and IV are specific examples of the inhibitory effects of compounds of the invention on T lymphocyte proliferative activity. As seen in Table III, compound (Ik) is inhibitory in a dose dependent manner with significant inhibition of T lymphocyte proliferation observed at concentrations ranging from 1 ug/ml to 100 ug/ml. Table IV demonstrates that compound (Ii) exerts significant, non dose dependent modulation of T lymphocyte proliferation with significant inhibition observed at all dose levels on the 1 ug/ml ConA cultures. The results shown in Table V indicate that methyl 1,3-O-isopropylidene-6-O-n-heptyl-α-D-fructofuranoside produced a dose-dependent, significant, inhibitory effect upon the ability of normal, splenically-derived, mouse T-cells to proliferate in response to mitogenic stimulation. There were less T-cells in the treated cultures at the end of the assay in comparison to the untreated control cultures.

TABLE II

EFFECT OF THE INVENTION ON A MIXED LYMPHOCYTE RESPONSE[a]

| Compound | Concentration of Con-A (ug/ml) | % Change from Control[b] Concentration of Invention (ug/ml) | | | | | | | |
|---|---|---|---|---|---|---|---|---|---|
| | | 100 | 25 | 10 | 2.5 | 1 | 0.1 | 0.01 | 0.01 |
| (Ib) | 4 | −99 | −86 | −76 | −68 | −67 | −45 | −35 | −25 |
| | 1 | −99 | −97 | −96 | −92 | −72 | −66 | −57 | −55 |
| (Ic) | 4 | −100 | −99 | −91 | −51 | −35 | −8 | 14 | −8 |
| | 1 | −100 | −99 | −79 | −21 | −19 | −3 | 8 | 11 |
| (Id) | 4 | −99 | −100 | −100 | −94 | −75 | −27 | −14 | −16 |
| | 1 | −99 | −100 | −100 | −91 | −67 | −25 | −10 | −9 |
| (Ie) | 4 | −100 | −99 | −92 | −79 | −59 | −9 | −4 | −8 |
| | 1 | −100 | −99 | −91 | −72 | −34 | −18 | −22 | −2 |
| (If) | 4 | −88 | −87 | −79 | −42 | −26 | −23 | 0 | −4 |
| | 1 | −4 | −85 | −74 | −25 | −14 | −2 | 6 | −8 |
| (Ig) | 4 | −100 | −77 | −73 | −20 | −5 | −9 | 12 | 7 |
| | 1 | −99 | −84 | −87 | −11 | −4 | −10 | 10 | −3 |
| (Ih) | 4 | −90 | −14 | −22 | 8 | 16 | 14 | 29 | 18 |
| | 1 | −74 | 39 | −4 | 63 | 61 | 29 | 32 | 12 |
| (Ii) | 4 | −47 | 7 | −1 | 22 | 17 | 28 | 37 | 28 |
| | 1 | −27 | 41 | 13 | 62 | 52 | 21 | 7 | 11 |
| (Ij) | 4 | −92 | −79 | −43 | −15 | 9 | −12 | 42 | −3 |
| | 1 | −100 | −100 | −100 | −100 | −100 | −100 | −100 | −60 |
| CSP | 4 | −94 | −74 | −74 | 68 | −68 | −57 | −25 | 5 |
| | 1 | −92 | −87 | −82 | −69 | −62 | 55 | −10 | 2 |
| AZT | 4 | −99 | −100 | −100 | −100 | −99 | −99 | −62 | −13 |
| | | −100 | −100 | −100 | −100 | −99 | −93 | −40 | −7 |

[a]Experimental compounds, cyclosporin (CSP) or AZT were suspended in DMSO (vehicle) diluted into medium. Normal spleen cells were cultured with 4 or 1 ug/ml Con-A together with various doses of experimental compound. The control contained medium with vehicle only. The effect of these compounds on the blastogenic response of spleen cells was determined by pulsing cells with $^3$H thymidine after 48 hours of culture and harvesting the cultures 18 hours thereafter.
[b]Results are expressed as percent change from the response of spleen cells cultured with control. NT = Not tested.

TABLE III

EFFECT OF COMPOUNDS ON THE CON-A RESPONSE OF NORMAL SPLEEN CELLS
Blastogenic response of normal spleen cells to Con-A × $10^{-3}$ cpm; % effect
Dose of DMSO in drug solution

| Compound | Con-A | 0.375% | 0.094% | 0.0375% | 9 × 3 × $10^3$% | 3.75 × $10^3$% | 3.75 × $10^{-4}$% | 3.75 × $10^{-5}$% | 3.75 × $10^{-6}$% |
|---|---|---|---|---|---|---|---|---|---|
| DMSO | 4 ug/ml | 166.1 ± 12.9 | 198.9 ± 6.6 | 194.4 ± 0.8 | 184.8 ± 1.8 | 209.0 ± 14.0 | 200.4 ± 21.9 | 186.6 ± 12.7 | 184.4 ± 19.8 |
| | 1 ug/ml | 109.9 ± 8.3 | 135 ± 4.6 | 128.7 ± 3.6 | 124.9 ± 3.9 | 147.0 ± 13.5 | 149.9 ± 4.0 | 135.9 ± 12.6 | 125.9.3 |
| | | 100 ug/ml | 25 ug/ml | 10 ug/ml | 2.5 ug/ml | 1 ug/ml | 0.1 ug/ml | 0.01 ug/ml | 0.001 ug/ml |
| (Ik) | 4 ug/ml | 0.4 ± 0.1 | 2.5 ± 0.4 | 18.4 ± 0.2 | 90.4 ± 7.8 | 135.3 ± 10.8 | 183.6 ± 10.4 | 212.6 ± 16.3 | 167.1 ± 16.7 |
| | | −100* | −99* | −91* | −51* | −35* | −8 | +14 | −8 |
| | 1 ug/ml | 0.3 ± 0.1 | 1.4 ± 0.2 | 27.4.1.3 | 98.5 ± 7.0 | 119.1 ± 3.3 | 145 ± 6.9 | 146.4 ± 5.2 | 139.5 ± 4.0 |
| | | −100* | −99* | −79* | −21* | −19* | −3 | +8 | +11 |

[a]Experimental compounds were suspended in DMSO and diluted into medium. Normal spleen cells were cultured with either 4 or 1 ug/ml Con-A together with various doses of experimental compound. The control contained medium with DMSO alone. The effect of these compounds on the blastogenic response of the spleen cells was assessed by pulsing the cells with $^3$H-thymidine after 48 hours of culture and harvesting the spleen cells 18 hours thereafter. Data are expressed as mean cpm of triplicates ± SD.
[b]The effect of experimental compounds on the blastogenic response of normal splenic T-lymphocytes is expressed as percent change from the response of spleen cells cultured in the presence of control. Significance of the effect of experimental compounds: *, $P < 0.001$; #, $P < 0.01$; **, $P < 0.005$.

TABLE IV

EFFECT OF COMPOUNDS ON THE CON-A RESPONSE OF NORMAL SPLEEN CELLS
Blastogenic response of normal spleen cells to Con-A × $10^{-3}$ cpm; % effect

| Compound | Con-A | Dose of DMSO in solution | | | | | | | |
|---|---|---|---|---|---|---|---|---|---|
| | | 0.375% | 0.094% | 0.0375% | 9 × 3 × $10^3$% | 3.7 × $10^3$% | 3.75 × $10^{-4}$% | 3.75 × $10^{-5}$% | 3.75 × $10^{-6}$% |
| DMSO | 4 ug/ml | 156 ± 8.7 | 143.6 ± 9.2 | 152.4 ± 9.1 | 157.3 ± 7.2 | 156.2 ± 10.7 | 149.4 ± 15.3 | 152.9 ± 5.8 | 155.8 ± 4.9 |
| | 1 ug/ml | 49.4 ± 1.8 | 42.4 ± 2.8 | 49.7 ± 5.1 | 43.5 ± 3.0 | 39.9 ± 2.6 | 45.4 ± 3.1 | 51.8 ± 2.9 | 57.1 ± 4.4 |
| | | Dose of compound added to blatogenesis assay: | | | | | | | |
| | | 100 ug/ml | 25 ug/ml | 10 ug/ml | 2.5 ug/ml | 1 ug/ml | 0.1 ug/ml | 0.01 ug/ml | 0.001 ug/ml |
| (Ii) | 4 ug/ml | 13.0 ± 1.7 | 30.0 ± 4.1 | 86.5 ± 9.2 | 134.1 ± 12.1 | 169.7 ± 5.2 | 130.7 ± 14.1 | 216.4 ± 2.7 | 151.2 ± 3.3 |
| | | (−92)* | (−79)* | (−43)* | (−15)* | (+9) | (−12) | (+42)* | (−3) |
| | 1 ug/ml | 0.1 ± 0.0 | 0.1 ± 0.0 | 0.1 ± 0.0 | 0.2 ± 0.2 | 0.1 ± 0.0 | 0.1 ± 0.0 | 0.1 ± 0.0 | 22.7 ± 1.6 |
| | | (−100)* | (−100)* | (−100)* | (−100)* | (−100)* | (−100)* | (−100)* | (−60)* |
| CSP | 4 ug/ml | 12.6 ± 1.6 | 48.5 ± 5.0 | 65 ± 4.3 | 103.9 ± 9.2 | 115.8 ± 7.8 | 112.9 ± 12.0 | 169.6 ± 1.4 | 155.6 ± 7.2 |
| | | (−92)* | (−66)* | (−57)* | (−34)* | (−26)* | (−24) | (+11)* | (0) |
| | 1 ug/ml | 3.8 ± 0. ± 0.1 | 9.2 ± 8.3 | 24.0 ± 3.4 | 16.9 ± 16.1 | 45.2 ± 2.2 | 40.9 ± 3.7 | 61.0 ± 3.5 | 57.9 ± 3.6 |
| | | (−92)* | (−78)* | (−50)* | (−61)* | (+16)* | (−10)* | (+18)* | (+1) |
| AZT | 4 ug/ml | 0.6 ± 0.1 | 1.3 ± 0.5 | 1.4 ± 0.4 | 1.9 ± 0.4 | 4.0 ± 1.5 | 24.5 ± 3.0 | 158.1 ± 11.3 | 163.7 ± 8.0 |
| | | (−100)* | (−99)* | (−99)* | (−99)* | (−97)* | (−84)* | (+3) | (+5) |
| | 1 ug/ml | 0.3 ± 0.0 | 0.5 ± 0.2 | 0.5 ± 0.1 | 0.7 ± 0.3 | 1.7 ± 0.1 | 9.1 ± 5.8 | 36.7 ± 3.1 | 47.1 ± 4.5 |

TABLE IV-continued

EFFECT OF COMPOUNDS ON THE CON-A RESPONSE OF NORMAL SPLEEN CELLS
Blastogenic response of normal spleen cells to Con-A × $10^{-3}$ cpm; % effect

| Compound | Con-A | | | | | | | |
|---|---|---|---|---|---|---|---|---|
| | | (−99)* | (−99)* | (−99)* | (−98)* | (−96)* | (−80)* | (29)* | (−18) |

<sup>a</sup>Experimental compounds, cyclosporin (CSP) or AZT were suspended in DMSO and diluted into medium. Normal spleen cells were cultured with either 4 or 1 ug/ml Con-A together with various doses of experimental compound. The control contained medium with DMSO alone. The effect of these compounds on the blastogenic response of the spleen cells was assessed by pulsing the cells with $^3$H-thymidine after 48 hours of culture and harvesting the spleen cells 18 hours thereafter. Data are expressed as cpm × $10^{-3}$ of triplicates ± SD.
<sup>b</sup>The effect of experimental compounds on the blastogenic response of normal splenic T-lymphocytes is expressed as percent change from the response of spleen cells cultured in the presence of control. Significance of the effect of experimental compounds: *, P < 0.001; #, P < 0.01; *, P < 0.05.

TABLE V

Effect of Methyl 1,3-0-Isopropylidene-6-0-N-heptyl-α, D-fructofuranoside, (Ia) on the Con-A Response of Normal Spleen Cells
Blastogenic response of normal spleen cells to Con-A × $10^{-3}$ cpm; % effect

| Compound | Con-A | | | | | | | | |
|---|---|---|---|---|---|---|---|---|---|
| None | 4 ug/ml | 84.5 ± 6.2 | | | | | | | |
| | 1 ug/ml | 55.4 ± 8.2 | | | | | | | |
| | | Dose of experimental compound added to blastogenesis assay: | | | | | | | |
| | | 100 ug/ml | 25 ug/ml | 10 ug/ml | 2.5 ug/ml | 1 ug/ml | 0.1 ug/ml | 0.01 ug/ml | 0.001 ug/ml |
| V | 4 ug/ml | 6.3 ± 2.2 | 13.7 ± 2.0 | 50.2 ± 3.4 | 63.8 ± 2.3 | 77.0 ± 4.2 | 88.8 ± 2.4 | 72.8 ± 0.8 | 68.7 ± 5.0 |
| | | −93** | −84** | −41** | −25# | −9 | +5 | −14* | −19* |
| | 1 ug/ml | 0.6 ± 0.1 | 1.5 ± 0.4 | 26.5 ± 8.8 | 47.2 ± 7.0 | 55.7 ± 8.4 | 71.1 ± 4.9 | 45.1 ± 4.9 | 52.6 ± 3.8 |
| | | −99** | −97** | −52* | −15 | +1 | +28* | −19 | −5 |
| Indo. | 4 ug/ml | 70.0 ± 5.6 | | | | | | | |
| | | −17* | | | | | | | |
| | 1 ug/ml | 57.7 ± 8.7 | | | | | | | |
| | | +4 | | | | | | | |
| MDGA | 4 ug/ml | 64.1 ± 9.2 | | | | | | | |
| | | −24* | | | | | | | |
| | 1 ug/ml | 47.6 ± 5.0 | | | | | | | |
| | | −14 | | | | | | | |

<sup>a</sup>Experimental compounds were suspended and diluted into medium. Normal spleen cells were cultured with either 4 or 1 ug/ml Con-A together with various doses of experimental compounds. The control contained medium alone. The effect of these compounds on the blastogenic response of the spleen cells was assessed by pulsing the cells with 3H-thymidine after 48 hours of culture and harvesting the spleen cells 18 hours thereafter. Data are expressed as cmp × $10^{-3}$ of triplicates ± SD.
<sup>b</sup>The effect of experimental compounds on the blastogenic response of normal splenic T-lymphocytes is expressed as per cent change from the response of spleen cells cultured in the presence of control. Significance of the effect of experimental compounds: *, P < 0.05; #P < 0.01; **, P < 0.0001.

Compounds of formula I were found to also be inhibitory to T lymphocyte activation, and proliferation when assessed for activity in mixed lymphocyte reactions. As is seen in Table VI, when compared to controls, fructofuranosides of formula I exhibit non dose dependent reductions in MLR generated proliferation with strong inhibition defined as greater than −50% of control cultures and moderate inhibition defined as −20% of controls.

Further immunomodulatory effects of compounds (Ia), (Id), and (Ie) were demonstrated by testing for inhibitory effects of these compounds on macrophage IL-1 production. In results given in Table VII, the compounds were observed to inhibit macrophage IL-1 production in a dose dependent manner with significant inventory effects observed in all compounds at concentrations ranging between 2.5 to 100 ug/ml.

In summary, compounds of formula I have been found to have immunomodulatory and anti-proliferative effects which predict that these compounds of the present invention have utility, from a therapeutic standpoint, in the treatment of a variety of inflammatory and/or autoimmune diseases.

TABLE VI

EFFECT OF THE INVENTION ON A MIXED LYMPHOCYTE RESPONSE<sup>a</sup>

| Compound | Concentration of Invention (um) | Mean O.D. Allogenic | Mean O.D. Syngeneic | % Change From Control<sup>b</sup> |
|---|---|---|---|---|
| Group A | | | | |
| Vehicle | | 0.311 | 0.199 | |
| Control A | | | | |
| (Ib) | 3 | 0.319 | 0.162 | −18 |
| | 10 | 0.382 | 0.194 | −2 |
| | 30 | 0.372 | 0.185 | −3 |
| | 100 | 0.353 | 0.223 | −32 |
| | 300 | 0.265 | 0.189 | −60 |
| (Ie) | 3 | 0.341 | 0.133 | 8 |
| | 10 | 0.318 | 0.130 | −2 |
| | 30 | 0.266 | 0.178 | −54 |
| | 100 | 0.216 | 0.146 | −64 |
| | 300 | 0.152 | 0.082 | −64 |
| (Ig) | 3 | 0.412 | 0.155 | 34 |
| | 10 | 0.421 | 0.182 | 24 |
| | 30 | 0.399 | 0.157 | 26 |
| | 100 | 0.419 | 0.173 | 28 |
| | 300 | 0.474 | 0.037 | 81 |
| (Ia) | 3 | 0.375 | 0.193 | −5 |
| | 10 | 0.361 | 0.175 | −3 |
| | 30 | 0.334 | 0.167 | −13 |
| | 100 | 0.429 | 0.192 | 23 |
| | 300 | 0.162 | 0.107 | −71 |
| Group B | | | | |
| Vehicle Control B | | 0.182 | 0.099 | |
| (Ic) | 3 | 0.207 | 0.096 | 34 |
| | 10 | 0.198 | 0.106 | 11 |
| | 30 | 0.200 | 0.148 | −37 |
| | 100 | 0.163 | 0.077 | 4 |
| | 300 | 0.034 | 0.159 | −251 |
| (If) | 3 | 0.195 | 0.140 | −34 |
| | 10 | 0.199 | 0.134 | −22 |

TABLE VI-continued
EFFECT OF THE INVENTION ON A MIXED LYMPHOCYTE RESPONSE[a]

| Compound | Concentration of Invention (um) | Mean O.D. Allogenic | Mean O.D. Syngeneic | % Change From Control[b] |
|---|---|---|---|---|
| | 30 | 0.199 | 0.164 | −58 |
| | 100 | 0.102 | 0.025 | −7 |
| | 300 | 0.032 | 0.022 | −88 |

[a]Experimental compounds were suspended in DMSO, diluted in medium and added at the indicated concentrations to mouse spleen cell mixed lymphocyte cultures. Vehicle control cultures contained medium plus the assay concentration of DMSO. The effect of the experimental compounds on the spleened T cell proliferative responses to both allogeneic and syngeneic (background proliferation) stimulators. T cell proliferative responses were determined after 5 days of culture by MTT reduction analysis with mean optical density (O.D.) corresponding to the amount of cellular proliferation in triplicate wells.
[b]Results are expressed as percentage change from the T cell proliferative response in vehicle control cultures.

The 3-substituted derivatives of glucofuranose and allofuranose are shown by the following general formula II:

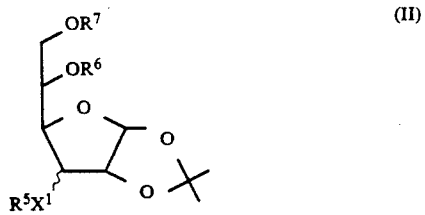

wherein:
$X^1$ is O and
$R^5$ is $C_{12}-C_{20}$ alkyl, or $C_nH_{2n}Y$, wherein n=1,2,3 or 4 and Y is selected from cyano, pyrrolyl, pyrrolidinyl, methylpyrrolidinyl, pipecolinyl, imidazolyl,

TABLE VII
EFFECT OF COMPOUNDS ON THE PRODUCTION OF INTERLEUKIN-1 BY PERITONEAL MACROPHAGES[a]

| | [3]H-Thymidine uptake by thymocytes; % effect | | | | | | | |
|---|---|---|---|---|---|---|---|---|
| Addition to thymocytes | 0.375% | 0.094% | 0.0375% | $9 \times 3 \times 10^3$% | $3.75 \times 10^3$% | $3.75 \times 10^{-4}$% | $3.75 \times 10^{-5}$% | $3.75 \times 10^{-6}$% |
| DMSO-PEC sup. | 8,693 ± 717 | 8,763 ± 344 | 10,117 ± 341 | 11,523 ± 1,442 | 11,027 ± 1,678 | 11,113 ± 1,616 | 10,873 ± 1,294 | 10,830 ± 1,144 |

| | Dose of experimental compound added to PEC cultures or control medium culture | | | | | | | |
|---|---|---|---|---|---|---|---|---|
| | 100 ug/ml | 25 ug/ml | 10 ug/ml | 2.5 ug/ml | 1 ug/ml | 0.1 ug/ml | 0.01 ug/ml | 0.001 ug/ml |
| (Ia) | 2,215 ± 643 | 3,210 ± 149 | 4,970 ± 410 | 8,250 ± 705 | 10,777 ± 1,903 | 10,265 ± 227 | 10,960 ± 1,748 | 10,550 ± 1,100 |
| PEC sup. | −75*[b] | −63* | −51* | −28* | −2 | −8 | +1 | −3 |
| (Id) | 1,930 − 479 | 2,537 ± 182 | 3,050 ± 191 | 6,400 ± 1,070 | 9,880 ± 1,029 | 13,190 ± 560 | 13,080 ± 282 | 10,850 ± 995 |
| PEC sup. | −78* | −71* | −70* | −44* | −10 | +19 | +20* | 0 |
| (Ie) | 4,300 ± 1,100 | 5,300 ± 1,405 | 6,100 ± 775 | 7,000 ± 686 | 9,710 ± 1,323 | 11,047 ± 702 | 12,040 ± 845 | 12,713 ± 866 |
| PEC sup. | −51* | −40* | −40* | −30* | −12 | −1 | +11 | +17 |

[a]Experimental compounds were suspended in DMSO and diluted into medium. They were then added to peritoneal exudate cells (PEC together with 10 ug/ml LPS. After 24 hr. culture supernatants were collected and then added for the subsequent 48 hr. to thymocytes and 1 ug/ml PHA. Thymocytes are used as indicators for I L-1 which selectively stimulates their growth. The effect of these compounds on thymocytes was measured by pulsing the cells with $^3$H-thymidine and harvesting the cells 18 hours thereafter. Data shown is mean cpm of triplicates ± SD. Shown in parenthesis is the percent effect of adding drug to PEC when compared to effect of PEC cultured without drug.
[b]Significance of the effect of drug: *, P < 0.001; *P < 0.01; *, P < 0.05.

A second embodiment of this invention are derivatives of glucose and allose. Glucose and allose are six carbon monosaccharides which differ from each other by the configuration of the 3-carbon in the sugar. More particularly, these compounds include monosubstituted ether derivatives of α-D or β-D glucofuranoses and α-D or β-D allofuranoses as well as analogs thereof. The generic formulae II and III, below, encompasses both α or β configurations. The compounds are substituted at the 3- or 6-position of the monosaccharide. The analogs of these compounds are those where the oxygen at the 3- or 6-position has been replaced by an amino group or by sulfur.

As will be apparent from the following discussion, the compounds of this embodiment can be broadly classified into two groups: fully blocked monosubstituted compounds, i.e., those having two isopropylidene protecting groups, and partially blocked monosubstituted compounds, i.e., those having only one isopropylidene protecting group. Applicants have found that fully blocked and partially blocked derivatives of glucofuranose and allofuranose are effective in the treatment of autoimmune and/or inflammatory disorders.

pyrazolyl, pyrazolinyl, pyrazolidinyl, oxazolyl, oxazolidinyl, isooxazolyl, isooxazolidinyl, imidazolidinyl, piperidinyl, piperazinyl, morpholinyl, $O(CH_2)_3N(CH_3)_2$, ($C_5-C_{10}$ alkoxy), $CH_2CH(CH_3)CH_2N(CH_3)_2$, $CH_2CH_2N(C_5-C_{10}$ alkyl)$_2$, or ($C_3-C_7$ alkenyl; or
$X^1$ is NH and
$R^5$ is $C_2-C_{10}$ alkyl, or
$C_nH_{2n}Y$ wherein n=1,2,3 or 4 and Y is selected from hydroxy, cyano, pyrrolyl, pyrrolidinyl methylpyrrolidinyl, pipecolinyl, imidazolyl, pyrazolyl, pyrazolinyl, pyrazolidinyl, oxazolyl, oxazolidinyl, isoxazolyl, isooxazolidinyl, imidazolidinyl, piperidinyl, piperazinyl, morpholinyl, $O(CH_2)_3N(CH_3)_2$, ($C_5-C_{10}$ alkoxy), and phenyl; and
$R^6$ and $R^7$ are hydrogen or form an isopropylidene ring.

Selective removal of the protecting group at the 5,6-Position by the following general procedure yields partially blocked compounds of formula II where $R^6$ and $R^7$ are hydrogen. Preferred compounds of formula II are:

1,2-O-Isopropylidene-3-O-n-dodecyl-α-D-
glucofuranose (IIa);

1,2-O-Isopropylidene-3-O-n-pentadecyl-α-D-
glucofuranose (IIb);

1,2-O-Isopropylidene-3-O-n-octodecyl-α-D-
glucofuranose (IIc);

1,2-O-Isopropylidene-3-O-3'-(phenylpropyl)-α-D-
glucofuranose (IId);

1,2:5,6-Di-O-isopropylidene-3-O-3'-(morpholinyl-
propyl)-α-D-glucofuranose (IIe);

1,2:5,6-Di-O-isopropylidene-3-O-3'-n-propoxy-n-hep-
tyl-α-D-glucofuranose (IIf);

1,2-O-Isopropylidene-3-O-3'-n-propoxy-n-heptyl-α-D-
glucofuranose (IIg);

1,2:5,6-Di-O-isopropylidene-3-O-2'-(ethylpyrrolidyl)-α-
D-glucofuranose (IIh);

1,2-O-Isopropylidene-3-O-2'-(ethylpyrrolidyl)-α-D-
glucofuranose (IIi);

1,2-O-isopropylidene-3-O-3'-(propan-1'-ol)-α-D-
glucofuranose (iij);

1,2:5,6-Di-O-isopropylidene-3-deoxy-3-amino-1'-(3'-
hydroxy-n-propyl)-α-D-glucofuranose (IIk);

1,2-O-isopropylidene-3-O-3'-(N',N'-dimethylamine-n-
propyl)-α-D-allofuranose (II1);

1,2:5,6-Di-O-isopropylidene-3-O-3'-(phenylpropyl)-α-
D-allofuranose (IIm);

1,2-O-Isopropylidene-3-deoxy-3-N-3'(N',N'-dime-
thylamino-n-propyl-α-D-allofuranose (IIn);

1,2-O-Isopropylidene-3-deoxy-3-amino-3-n-heptyl-α-
D-allofuranose (IIo);

1,2-O-isopropylidene-3-deoxy-3-amino-3'-(propan-1-
ol)-α-D-glucofuranose (IIp);

1,2-O-Isopropylidene-3-deoxy-3-N-3'-(phenylpropyl)-
α-D-allofuranose (IIq);

1,2-O-isopropylidene-3-deoxy-3-amino-n-heptyl-α-D-
glucofuranose (IIr); and 1,2-O-Isopropylidene-3-deoxy-3-amino-n-3'-(phenyl-
propyl)-α-D-glucofuranose (IIs).

Representative examples of the above.-mentioned compounds of formula II were prepared by one of the following procedures in Examples 6–11. The pharmacological activity of the compounds of formula II is illustrated in Example 12.

EXAMPLE 6

General Procedure for the Selective Hydrolysis of 5,6-positions.

The fully blocked monosaccharide (1.0 g) is dissolved in tetrahydrofuran (1 ml) and to this was added dropwise a perchloric acid solution (30%, 1 ml), with stirring, at 0°-5° C. The reaction is monitored by TLC and GC. The normal reaction time varies from 20 minutes to 1 hour. After the completion of the reaction, it is neutralized with a saturated solution of potassium carbonate to a pH of 9.0. The solid salt formed is filtered through Celite and washed well with tetrahydrofuran (50 ml) in several portions. The combined filtrate is subjected to rotary evaporation and the residue obtained is purified by flash chromatography using silica gel and appropriate solvents. The yield of the final products varies from 75-98%.

EXAMPLE 7

Preparation of
1,2:5,6-di-O-isopropylidene-3-O-n-dodecyl-α-D-
glucofuranose and
1,2-O-isopropylidene-3-O-n-dodecyl-α-D-
glucofuranose, (IIa).

Step 1:
1,2:5,6-Di-O-isopropylidene-3-O-n-dodecyl-α-D-
glucofuranose ($R^5 = C_{12}H_{25}$).

A mixture of 1,2:5,6-Di-O-isopropylidene-α-D-glucofuranose (5.2 g; 0.02 mol) and dry powdered sodium hydroxide (3 equivalents) was heated together at 120°-130° in an oil bath. This reaction was conducted under diminished pressure so as to get rid of water formed during the reaction. This reaction takes about 30–45 minutes depending upon the batch size. The vacuum line was then disconnected and 1-bromododecane (1.2 eq.) was added in one portion. The reaction mixture was stirred at the same temperature for 30 minutes to 2 hours. The reaction flask was then cooled, dichloromethane (100 ml) was added and the mixture was filtered through Celite and washed with 100 ml more of the solvent. Solvent was removed using rotary evaporator and the residue purified by flash chromatography using ether: hexane (10:90).

Step 2: Hydrolysis according to the general procedure described in Example 6 gave the partially blocked compound
1,2-O-isopropylidene-3-O-n-dodecyl-α-D-
glucofuranose, (IIa).

Example 8

Preparation of
1,2:5,6-Di-O-isopropylidene-3-O-3'(n-propoxyheptyl)-
α-D-glucofuranose, (IIf) and
1,2-O-Isopropylidene-3-O-3'-(n-propoxy-heptyl)-α-D-
glucofuranose, (IIg).

Step 1: Preparation of
1,2:5,6-Di-O-isopropylidene-3-O-3'(n-propoxyheptyl)-
α-D-glucofuranose ($R^5 = -(CH_2)_3OC_7H_{15}$)

1,2:5,6-Di-O-isopropylidene-3-O-3'-propanol-α-D-glucofuranose was prepared by reacting 1,2:5,6-di-O-isopropylidene-α-D-glucofuranose with sodium hydroxide (equivalents) at 120°-130° C. under vacuum. After 30 minutes, the vacuum line was disconnected and 1-bromopropanol (3 eq) was added. The reaction mixture was heated at the same temperature for 45 minutes. The flask was then cooled and ether added (100 mL). The solution was filtered through Celite, washed with 100 mL more of ether and the solvent removed. The residue was purified by flash chromatrography using 10% ether in hexane to afford the title compound in 84% yield.

A mixture of 1,2:5,6-Di-O-isopropylidene-3-O-3'-propanol-α-D-glucofuranose (0.02 mole) and dry powdered sodium hydroxide (3 equivalents) was heated at 120-1300 under vacuum. When the evolution of water had ceased, the vacuum line was disconnected and heptyl bromide (1.2 eq.) was added in one portion and the mixture heated at the same temperature for 1 hour. The reaction flask was cooled and ether (100 ml) was added. The solution was filtered through Celite and washed with 100 ml of ether. The combined solvents were subjected to rotary evaporation to remove the ether and then purified by flash chromatography using 5% ether in hexane. 1,2:5,6-Di-O-isopropylidene-3-O-3'(n-propoxyheptyl)-α-D-glucofuranose was obtained and characterized by NMR and mass spectral analysis.

Step 2: Hydrolysis according to the general procedure described in Example 6 gave the partially blocked compound 1,2-O-Isopropylidene-3-O-3'-(n-propoxyheptyl)-α-D-glucofuranose.

EXAMPLE 9

Preparation of 1,2-O-Isopropylidene-3-deoxy-3-amino or substituted amino-α-D-glucofuranoses.

Step 1: Preparation of 1,2:5,6-di-O-isopropylidene-3-deoxy-3-azido-α-D-glucofuranose A mixture of 1,2:5,6-di-O-isopropylidene-3-tosyl-α-D-allofuranose (prepared as described in Methods in Carbohydrate Chemistry, vol. 6, p. 197 (20 g) and sodium azide (2.5-equivalents) in anhydrous DMF (100 ml) was heated at 80° C. for 3 hours. The progress of the reaction was monitored by TLC and GC. When the reaction was complete, DMF was removed under reduced pressure and the residue was extracted with ether (150 ml), and washed with water (2×25 ml), saturated solution of sodium bicarbonate (2×20 ml) and then with brine (1×25 ml). The organic layer was dried over MGSO4, filtered and solvent was removed using a rotary evaporator. This compound (95% yield) was found to be sufficiently pure by TLC and GC and hence was used in the next step.

Step 2: Preparation of 1,2:5,6-di-O-isopropylidene-3-deoxy-3-amino-α-D-glucofuranose.

The azido compound (5 g) obtained in step 1 was reduced catalytically using H2, Palladium-charcoal (10%, 50 mg) and methanol (100 ml) in a Parr-hydrogenator at a pressure of 35 psi for 6 hours. The reaction mixture was then filtered using Celite, washed with methanol (100 ml) and the solvent removed using a rotary evaporator. The residue obtained showed a single homogenous spot on TLC and complete disappearance of azido group peak by IR. The yield of the pure compound was 95%.

Step 3: Hydrolysis according to the general procedure described in Example 6 gave the partially blocked compound 1,2-di-O-isopropylidene-3-deoxy-3-amino-α-D-glucofuranose.

Step 4: Preparation of 1,2:5,6-Di-O-isopropylidene-3-deoxy-3-amino-n-heptyl-α-D-glucofuranose.

3-Deoxy-3-amino compound obtained in step 3 was heated with 1-bromoheptane at 70°-80° C. in the ratio of 1:2.2 for 3-4 hours. The progress of the reaction was followed by TLC and GC. After the completion of the reaction, the product was extracted with ethyl acetate, washed with a saturated solution of sodium bicarbonate, brine and then the organic layer dried over anhydrous MgSO4. The removal of the solvent gave the crude compound which was purified by flash chromatography. Other amino substituents can be synthesized by the same procedure using an appropriate alkyl halide compound. The alkyl halide itself can be further functionalized.

Step 4: Hydrolysis according to the general procedure described in Example 6 gave the partially blocked compound 1,2-Di-O-isopropylidene-3-deoxy-3-amino-n-heptyl-α-D-glucofuranose, (IIr)

EXAMPLE 10

Preparation of 1,2:5,6-Di-O-isopropylidene-3-O-substituted α-D-allofuranoses and 1,2-O-Isopropylidene-3-O-substituted α-D-allofuranose.

Step 1: 1,2:5,6-di-O-isopropylidene-α,D-allofuranose was treated with dry powdered sodium hydroxide and a suitable alkyl halide or substituted alkyl halide in the same manner and ratio as described for the glucofuranose derivative in Example 7, step 1.

Step 2: Hydrolysis according to the general procedure described in Example 6 gave the partially blocked compounds.

EXAMPLE 11

Preparation of 1,2:5,6-Di-O-isopropylidene-3-deoxy-3-amino-n-heptyl-α-D-allofuranose and 1,2-O-Isopropropylidene-3-deoxy-3-amino-n-heptyl-α-D-allofuranose, (IIo).

Step 1: Preparation of 1,2:5,6-Di-O-isopropylidene-3-deoxy-3-amino-n-heptyl α-D-allofuranose. 1,2:5,6-Di-O-isopropylidene-α-D-ribo-hexofuranose-3-ulose (prepared according to the literature procedure "Methods in Carbohydrate Chemistry, Vol. VI pp. 125) and heptylamine, in the ratio of 1:2, were mixed and heated at 50°-80° C. for 30 minutes to 2 hours under diminished pressure. When the evolution of water had ceased (the progress of the reaction was monitored by TLC and GC), the vacuum line was disconnected. The product was dissolved in anhydrous THP and added dropwise to a stirred suspension of lithium aluminum hydride (LAH, 2 equivalents) in anhydrous THF. The reaction was carried out at 5°-100° C. with rigorous stirring and was complete in 2 to 3 hours. The excess LAH was then decomposed by careful addition of water and 15% sodium hydroxide solution (1 ml of each per gram of LAH used). The reaction mixture was then filtered through Celite, washed with THF and solvent removed. The residue was dissolved in ethylacetate, washed with water, dried and solvent removed. It was purified by flash chromatography using appropriate solvents. Other amino substituted compounds can be prepared by substituting other appropriate &mine compounds for heptylamine in this procedure.

Step 2: Hydrolysis according to the general procedure described in Example 6 gave the partially blocked compound 1,2-O-isopropylidene-3-deoxy-3-amino-n-heptyl-α-D-allofuranose, (IIq). (IIq).

EXAMPLE 12

Pharmacological Activity of Compounds of Formula II

Compounds were tested for immunomodulatory, anti-proliferative and anti-inflammatory activities in screening assays which measure T-cell proliferation, activation and macrophage IL-1 production as described in Example 5. Compounds of the present invention were also tested for effects on fibroblast proliferation and production of pro-inflammatory mediators.

Since the early 1970's it has been known that important mediators of the inflammatory process are the leukotrienes and prostaglandins which are synthesized by tissue cells and macrophages at the site of inflammation (Flower et al., Analgesics-antipyretics and Anti-inflammatory Agents; Drugs Employed in the Treatment of Gout," *The Pharmacological Basis of Therapeutics*, New York, 1985). In inflammatory disorders damage to mammalian cells occurs by physical trauma or the combination of an antigen with antibody and this is thought to initiate the biosynthesis of these mediators of inflammation, which are, in turn, responsible for the physiological and visible signs of inflammation. This correlates with the recruitment, activation and proliferation of T-lymphocytes to the localized area of inflammation. In psoriasis, there is an increase in the formation of arachidonic acid in the psoriatic skin that results in mildly increased production of prostaglandins, and a severalfold increase in the concentration of leukotrienes, principally $LTB_4$. $LTB_4$ is the principal biological mediator which is responsible for the promotion of the inflammatory process that exacerbates the disease (Anderson, T. F., "New Reasons for Using Time-Honored Empiric Therapy," *Consultant*, 1985. In the autoimmune diseases with arthritic components, proliferating synovial fibroblasts are responsible for the production of inflammation mediators. The data below demonstrates that the compounds of the present invention have pharmacological activity in reducing fibroblast production of $LTB_4$ and $PGE_2$, which have an effect in regulating the activity of the infiltrating T-lymphocytes, and are antiproliferative agents in skin fibroblast cultures. Moreover, this activity indicates that physiologically acceptable doses of these claimed compounds can be used, either topically or systemically, to inhibit T-cell and human fibroblast proliferation.

Assays were conducted to demonstrate the ability of the compounds of the present invention to modulate the proliferation of BUD-8 human skin fibroblasts and to modulate the production of $PGE_2$ and $LTB_4$.

Specific Method: Fiberblast Assay

The human skin cell fibroblast line, BUD-8 was obtained prior to each assay from the American Type Culture Collection. This is a fibroblast-like cell line which was originally derived from the normal skin of a 56 year old white female.

BUD-8 cell cultures were expanded for use in 25 cm$^2$ flasks at 37° C. in an atmosphere of 5% $CO_2$ in air. At approximately 4-5 five day intervals, or when confluence was reached, the cells were passaged. This was accomplished by detaching the cells with a Teflon scraper, washing and reseeding the cells at a lower density into fresh tissue culture flasks.

The effect of the compound of the present invention on the proliferative capacity of human BUD-8 skin fibroblasts was measured with the use of a $^3$H-thymidine incorporation assay using culture conditions which were similar to those used for a Con-A blastogenesis assay, described previously. Cultured skin cells were detached from the surface of tissue culture flasks mechanically with a Teflon scraper. The cells were washed, resuspended in incubation medium and the viabilities were determined. These cells were then plated in triplicate at a density of $2 \times 10^3$ cells/0.1 ml/microtiter well for the proliferation assay and a density of $1 \times 10^4$ cells/0.1 ml/microtiter well for the assays to quantitate $PGE_2$ and $LTB_4$. To these cells was added incubation medium containing indomethacin to inhibit prostaglandin production, or nordihydroguaiaretic acid (NDGA) to inhibit leukotriene production (positive controls).

After 18 hours of culture, samples of the BUD-8 skin cell supernatants were collected from one set of microtiter plates and frozen until assayed for $PGE_2$ or for $LTB_4$ content using the radioimmunoassays described below.

After 3 days of culture, 1 uCi $^3$H-thymidine was added in a 50 ul volume to each culture well of the microtiter plates. Eighteen hours later, each of the BUD-8 cultures was examined morphologically for evidence of compound-induced toxicity such as cell rounding or granularity. The thymidine-pulsed cells were then precipitated and the amount of $^3$H-thymidine incorporated was counted in a liquid scintillation counter.

The concentrations of the compounds of the invention which were used in these assays were:

| Group 1: | 0 ug/ml | Group 5: | 100 ug/ml |
|---|---|---|---|
| Group 2: | 1 ug/ml | Group 6: | 300 ug/ml |
| Group 3: | 10 ug/ml | Group 7: | 750 ug/ml |
| Group 4: | 25 ug/ml | | |

The incubation medium used for culturing the BUD-8 cells was RPMI-1640 medium containing 10% fetal bovine serum, 100 ug/ml streptomycin, 100 U/ml penicillin, 0.2M Hepes buffer solution, $5 \times 10^{-5}$ M 2-mercaptoethanol and 2 mM glutamine.

A radioinmunoassay (New England Nuclear) was used to quantitate $PGE_2$ levels in BUD-8 skin cell culture supernatants. Briefly, into each polypropylene tube were mixed 0.1 ml anti-$PGE_2$, 0.1 ml $^{125}$I-$PGE_2$ and 0.1 ml $PGE_2$ standard or $PGE_2$ containing sample. The BUD-8 skin culture supernatants were diluted 1:2 prior to addition to the radioimmunoassay. Tubes were refrigerated overnight. A polyethylene glycol solution (16%, 6,000 m.w.) was then added to precipitate immune complexes and the radioactivity in the precipitate was counted in a gamma counter.

Levels of $LTB_4$ in aliquots of BUD-8 skin cell cultures supernatants were quantitated by radioimmunoassay (New England Nuclear). Briefly, into each polyproplyene tube were mixed 0.1 ml anti-$LTB_4$, 0.1. ml $^3$H-$LTB_4$ and 0.1 ml $LTB_4$ standard or $LTB_4$ containing sample. The BUD-8 skin cell culture supernatants were used directly in the radioimmunoassay. Tubes were refrigerated overnight. A charcoal solution (0.5 ml of 0.5% charcoal Norit A) was added and each tube was centrifuged. The radioactivity in the supernatant was then counted in a liquid scintillation counter.

The Student's t test was used to determine the significance of the difference between values for T-lymphocytes or skin cells cultured in the presence of experimental compounds versus in control medium alone.

The inhibitory effects of compounds (IIa), (IIg), and (IIk) on the T lymphocyte blastogenic response to ConA are illustrated in Table VIII. These compounds were found to exhibit non-dose dependent inhibition of T lymphocyte proliferation with all compounds tested being strongly inhibitory (greater than $-50\%$ of control response) at the 100 ug/ml concentration of compound. A specific example of a compound of the present invention mediated modulation of the T lymphocyte proliferative response to ConA is given in Table IX.

Statistically significant inhibition of T cell proliferation was exerted by compound (IIg) at concentrations ranging between 100 and 750 ug/ml.

Further immunomodulatory effects of these compounds were demonstrated in the MLR assay (Table X). Strong non-dose dependent inhibition (greater than −50% of control) was observed at several concentrations of compounds (IIg) and (IIa). This indicates that the compounds inhibit T lymphocyte function in activated cultures.

TABLE VIII

EFFECT OF THE INVENTION ON THE CON-A RESPONSE OF NORMAL SPLEEN CELLS[a]

| Compound | Concentration of Con-A (ugg/ml) | % Change from Control[b] Concentration of Invention (ug/ml) | | | | | | |
|---|---|---|---|---|---|---|---|---|
| | | 750 | 300 | 100 | 25 | 10 | 2.5 | 1 |
| (IIg) | 4 | −79 | −91 | 068 | 123 | 73 | NT | 80 |
| | 1 | −82 | −84 | −67 | 51 | 39 | NT | 27 |
| (IIa) | 4 | NT | NT | −100 | −94 | −83 | −50 | −33 |
| | 1 | NT | NT | −100 | −99 | −95 | −60 | −21 |
| (IIk) | 4 | NT | NT | −83 | −5 | −4 | 0 | −5 |
| | 1 | NT | NT | −95 | −45 | −38 | −31 | −20 |
| CSP | 4 | NT | NT | −92 | −66 | −57 | −34 | −26 |
| | 1 | NT | NT | −92 | −78 | −50 | −61 | −16 |
| AZT | 4 | NT | NT | −100 | −99 | −99 | −99 | −97 |
| | 1 | NT | NT | −99 | −99 | −99 | −98 | −96 |

[a]Experimental compounds, cyclosporin (CSP) or AZT were suspended in DMSO (vehicle) diluted into medium. Normal spleen cells were cultured with 4 or 1 ugg/ml Con-A together with various doses of experimental compound. The control contained medium with vehicle only. The effect of these compounds on the blastogenic response of spleen cells was determined by pulsing the cells with $^3$H-thymidine after 48 hours of culture and harvesting the culture 18 hours therafter.
[b]Results are expressed as percent change from the response of spleen cells cultured with control. NT = not tested

TABLE IX

EFFECT OF EXPERIMENTAL COMPOUNDS ON THE CON-A RESPONSE OF NORMAL SPLEEN CELLS[a]
Blastogenic response of normal spleen cells to Con-A; % effect

| Compound | Con-A | | | | | | |
|---|---|---|---|---|---|---|---|
| control | 4 ug/ml | 97,141 ± 5,802 | | | | | |
| | 1 ug/ml | 72,234 ± 6,650 | | | | | |
| | | Dose of experimental compound added to blastogenesis assay: | | | | | |
| | | 750 ug/ml | 300 ug/ml | 100 ug/ml | 25 ug/ml | 10 ug/ml | 1 ug/ml |
| (IIg) | 4 ug/ml | 20,265 ± 12,455 | 8,268 ± 322 | 31,073 ± 10,784 | 216,784 ± 27,862 | 168,131 ± 14,911 | 174,764 ± 29,872 |
| | | −79** | −91** | −68** | +123# | +73# | +80* |
| | 1 ug/ml | 12,807 ± 9,049 | 11,212 ± 15,288 | 23,806 ± 1,727 | 108,874 ± 15,534 | 100,734 ± 25,985 | 91,958 ± 15,723 |
| | | −82** | −84# | −67** | +51# | +39 | +27 |

[a]Experimental compounds were first suspended in DMSO or ethanol, then diluted into medium and added at various concentrations to normal spleen cells and either 4 or 1 ug/ml Con-A. Control cultures contained comparable concentrations of DMSO or ethanol. The effect of these compounds on the blastogenic response of the spleen cells was assessed by pulsing the cells with $^3$-H-thymidine after 48 hours of culture and harvesting the spleen cells 18 hours thereafter. Data are expre ssed as cpm of triplicates ± SD.
[b]The effect of experimental compounds on the blastogenic response of normal splenic T-lymphocytes is expressed as percent change from the response of spleen cells cultured in the absence of experimental compounds. Significance of the effect of experimental compounds: *, $P < 0.05$; #, $P < 0.01$; **, $P < 0.001$.

TABLE X

EFFECT OF THE INVENTION ON A MIXED LYMPHOCYTE RESPONSE[a]

| Compound | Concentration of Invention (ugm) | Mean O.D. Allogenic | Mean O.D. Syngeneic | % Change From Control[b] |
|---|---|---|---|---|
| Group A | | | | |
| Vehicle Control A | | 0.245 | 0.075 | 13 |
| (IIg) | 3 | 0.137 | 0.078 | −61 |
| | 10 | 0.197 | 0.070 | −15 |
| | 30 | 0.171 | 0.075 | −36 |
| | 100 | 0.057 | 0.058 | −101 |
| | 300 | 0.026 | 0.022 | −97 |
| Group B | | | | |
| Vehicle Control B | | 0.182 | 0.099 | |
| (IIa) | 3 | 0.184 | 0.117 | −19 |
| | 10 | 0.185 | 0.135 | −40 |
| | 30 | 0.158 | 0.056 | 23 |
| | 100 | 0.024 | 0.012 | −86 |
| | 300 | 0.025 | 0.022 | −96 |

[a]Experimental compounds were suspended in DMSO, diluted in medium and added at the indicated concentrations to mouse spleen cell mixed lymphocyte cultures. Vehicle control cultures contained medium plus the assay concentration of DMSO. The effect of the experimental compounds on the spleened T cell proliferative responses to both allogeneic and syngeneic (background proliferation) stimulators. T cell proliferative responses were determined after 5 days of culture by MTT reductio n analysis with mean optical density (O.D.) corresponding to the amount of cellular proliferation in triplicate wells.
[b]Results are expressed as percentage change from the T cell proliferative response in vehicle control cultures.

Mouse peritoneal macrophage IL-1 production was also found to be inhibited by compounds of the present invention as described in Table XI. Compound (IIg) exerted dose dependent inhibition of macrophage IL-1 production with significant decreases in IL-1 activity observed at 10, 25 and 100 ug/ml of compound. Since IL-1 is a potent stimulator of B and T lymphocytes, both of which are active in inflammatory and autoimmune diseases, these data are indicative of the extensive immunomodulatory effects of the compounds of the present invention. Because uncontrolled fibroblast proliferation and biosynthetic activity are hallmarks of inflammatory diseases in which joint damage is observed (such as rheumatoid arthritis), compounds of the present invention were tested for activity in fibroblast cultures. Studies were performed to determine the anti-proliferative effects of the compounds, and these effects were correlated with levels of the pro-inflammatory mediators $PGE_2$ and $LTB_4$ in the fibroblast cultures.

Compounds of the present invention were also tested for potential effects on fibroblast proliferative and biosynthetic activity. Compound (IIg) was observed to exert non dose dependent anti-proliferative effects on Bud-8 skin cell fibroblasts with significant anti-proliferative activity seen at 100, 25 and 10 ug/ml of compound (Table XII). Evidence of cell toxicity was observed at the two highest concentrations of compound tested.

This anti-proliferative effect correlated well with significant non dose dependent inhibitory effects on fibroblast production of pro-inflammatory mediators.

$LTB_4$ levels were significantly decreased in Bud 8 skin cell cultures at concentrations of 1–100 ug/ml of compound (IIg) (Table XIII). Cell toxicity was again observed in cultures which included 300 and 750 ug/ml of the compound. Non dose dependent inhibitory effects on fibroblast $PGE_2$ production are exhibited in Table XIV where concentrations of 1, 10 and 25 ug/ml of compound are seen to correlate with significant decreases in $PGE_2$ levels in Bud 8 skin cell fibroblasts cultures. Compound induced cell toxicity was observed only at the highest dose level tested.

Since uncontrolled fibroblast proliferation and activation are dominant features in inflammatory diseases such as rheumatoid arthritis and psoriasis, these data strongly suggest the potential for the use of the compounds of the present invention as therapeutic agents for the treatment of these diseases.

TABLE XI

EFFECT OF COMPOUNDS ON THE PRODUCTION OF INTERLEUKIN-1 BY PERITONEAL MACROPHAGES

| | $^3$H-Thymidine uptake by thymocytes; % effect | | | | | | | |
|---|---|---|---|---|---|---|---|---|
| Addition to thymocytes | 0.375% | 0.094% | 0.0375% | $9 \times 3 \times 10^3$% | $3.75 \times 10^3$% | $3.75 \times 10^{-4}$% | $3.75 \times 10^{-5}$% | $3.75 \times 10^{-6}$% |
| DMSO-PEC sup. | 6,739 ± 397 | 7,662 ± 798 | 7,679 ± 402 | 8,345 ± 617 | 7,086 ± 625 | 7,720 ± 886 | 8,223 ± 483 | 8,202 ± 206 |

| | Dose of experimental compound added to PEC cultures or control medium culture | | | | | | | |
|---|---|---|---|---|---|---|---|---|
| | 100 ug/ml | 25 ug/ml | 10 ug/ml | 2.5 ug/ml | 1 ug/ml | 0.1 ug/ml | 0.01 ug/ml | 0.001 ug/ml |
| (IIg) PEC sup. | 934 ± 43 (−80)* | 3,265 ± 141 (−57)* | 4,854 ± 471 (−37)* | 7,229 ± 471 (−13) | 7,307 ± 680 (−6) | 8,790 ± 533 (+14) | 7,873 ± 379 (−4) | 8,823 ± 771 (+8) |

$^a$Experimental compounds, cyclosporin (CSP) or AZT were suspended in DMSO and diluted into medium. They were then added to peritoneal exudate cells (PEC) together with 10 ug/ml LPS. After 24 hr. culture supernatants were collected and added for the subsequent 48 hr. to thymocytes and 1 ug/ml PHA. Thymocytes are used as indicators for IL-1 which selectively stimulates their growth. The effect of these compounds on thymocytes was measured by pulsing the cells with $^3$H-thymidine and harvesting the cells 18 hours thereafter. Data shown is mean cpm of triplicates ± SD. Shown in parenthesis is the percent effect of adding drug to PEC when compared to effect of PEC cultured without drug.
$^b$Significance of the effect of drug: *, $P < 0.001$; *P $< 0.01$; *, $P < 0.05$.

TABLE XII

EFFECT OF COMPOUNDS ON THE PROLIFERATION OF BUD-8 SKIN CELL FIBROBLASTS$^a$

| Compound | | | | | | |
|---|---|---|---|---|---|---|
| | $^3$H-Thymidine uptake by BUD-8 skin cells); % Effect | | | | | |
| none | 6,164 ± 469 | | | | | |
| | Dose of experimental compound added to BUD-8 skin cells: | | | | | |
| | 750 ug/ml | 300 ug/ml | 100 ug/ml | 25 ug/ml | 10 ug/ml | 1 ug/ml |
| (IIg) | 3,898 ± 1,692 −37$^c$ | 2,233 ± 244 −64**$^c$ | 4,117 ± 481 −33# | 4,207 ± 450 −32# | 3,552 ± 994 −42# | 6,096 ± 1,352 −1 |

$^a$Experimental compounds were first suspended in DMSO or ethanol, then diluted into medium and added at various concentrations to human BUD-8 skin cell fibroblasts. Control cultures contained comparable concentrations of DMSO or ethanol. The effect of these compounds on the proliferation of the BUD-8 skin cells was assessed by pulsing the cells with $^3$H-thymidine after 72 hours of culture and harvesting the BUD-8 cells 18 hours thereafter. Data are expressed as cpm of trip licates ± SD.
$^b$The effect of experimental compounds on the proliferation of BUD-8 cells is expressed as per cent change from the amount of $^3$H-thymidine incorporated in the absence of experimental compounds. Significance of the effect of experimental compounds: *, $P < 0.05$; #, $P < 0.01$; **, $P < 0.001$.
$^c$Evidence of toxicity of compound on BUD-8 cells on the basis of either cell rounding or granularity.

TABLE XIII

EFFECT OF COMPOUNDS ON THE PRODUCTION OF $LTB_4$ BY BUD-8 SKIN CELL FIBROBLASTS$^a$

| Compound | | | | | | |
|---|---|---|---|---|---|---|
| | pg $LTB_4$/1000 ul supernatant ($LTB_4$ produced/$10^5$ BUD-8 cells); % Effect | | | | | |
| control | 38.8 ± 1.6 (749) | | | | | |
| | Dose of compound added to BUD-8 skin cells; | | | | | |
| | 750 ug/ml | 300 ug/ml | 100 ug/ml | 25 ug/ml | 10 ug/ml | 1 ug/ml |
| (IIg) | 19.3 ± 1.9 −50**$^c$ | 24.5 ± 2.8 −37#$^c$ | 27.3 ± 2.6 (520) −30# | 23.7 ± 0.5 (447) −39** | 28.8 ± 1.4 (550) −26# | 32.2 ± 1.9 (619) −17# |

$^a$Experimental compounds were first suspended in DMSO or ethanol, then diluted into medium and added at various concentrations to human BUD-8 skin cell fibroblasts. The effect of these compounds on BUD-8 cell production of $LTB_4$ was assessed by radioimmunoassay. All values are the results of triplicate determinations. Data are expressed as pg $LTB_4$ in 100 ul supernatant ± SD. In parentheses is the calculated pg $LTB_4$ secreted per $10^5$ cells.
$^b$The effect of experimental compounds on the amount of $LTB_4$ in the supernatants of BUD-8 skin cells is expressed as per cent change from the amount of $LTB_4$ of cells cultured in the absence of experimental compounds. Significance of the effect of experimental compounds: *, $P < 0.05$; #, $P < 0.01$; **, $P < 0.001$.
$^c$Evidence of toxicity of compound on BUD-8 cells on the basis of either cell rounding or granularity.

TABLE XIV

EFFECT OF COMPOUNDS ON THE PRODUCTION OF $PGE_2$ BY BUD-8 SKIN CELL FIBROBLASTS[a]

| Compound | | | | | | |
|---|---|---|---|---|---|---|
| | pg $PGE_2$/50 ul supernatant ($PGE_2$ produced/$10^5$ BUD-8 cells); % Effect | | | | | |
| control | 9.4 ± 1.1 (325) | | | | | |
| | Dose of experimental compound added to BUD-8 skin cells: | | | | | |
| | 750 ug/ml | 300 ug/ml | 100 ug/ml | 25 ug/ml | 10 ug/ml | 1 ug/ml |
| (IIg) | 7.3 ± 0.2 (241) | 19.6 ± 1.6 (731) | 11.0 ± 1.4 (388) | 4.1 ± 0.3 (111) | 5.6 ± 0.4 (173) | 5.2 ± 0.9 (157) |
| | −22*[c] | 108** | +17 | −57# | −40# | −45# |

[a]Experimental compounds were first suspended in DMSO or ethanol, then diluted into medium and added at various concentrations to human BUD-8 skin cell fibroblasts. The effect of these compounds on BUD-8 cell production of $PGE_2$ was assessed by radioimmunoassay. All values are the results of triplicate determinations. Data are expressed as pg $PGE_2$ in 50 ul supernatant ± SD. In parentheses is the calculated pg $PGE_2$ ecreted per $10^5$ cells.

[b]The effect of experimental compounds on the amount of $PGE_2$ in the supernatants of BUD-8 skin cells is expressed as per cent change from the amount of $PGE_2$ of cells cultured in the absence of experimental compounds. Significance of the effect of experimental compounds: *, $P < 0.05$; #, $P < 0.01$; **, $P < 0.001$.

[c]Evidence of toxicity of compound on BUD-8 cells on the basis of either cell rounding or granularity.

The fully blocked 6-substituted derivatives of glucofuranose and allofuranose are shown by the following general formula III:

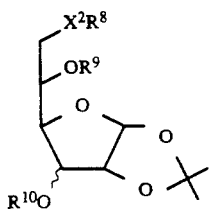

(III)

wherein $X^2$ is O,
$R^8$ is $C_8$–$C_{20}$ alkyl, or $C_nH_{2n}Y$, wherein n=1,2,3, or 4 and
Y is selected from phenyl, cyano, pyrrolyl, methylpyrrolidinyl, pipecolinyl, imidazolyl, pyrazolyl, pyrazolinyl, pyrazolidinyl, oxazolyl, oxazolidinyl, isooxazolyl, isoozazolidinyl, imidazolidinyl, piperidinyl, piperazinyl, morpholinyl, $O(CH_2)_3N(CH_3)_2$, ($C_5$–$C_{10}$ alkoxy), NH or $N(CH_3)_2$; or
$X^2$ is NH and
$R^8$ is H, or $C_nH_{2n}Y$, wherein n=1,2,3 or 4 and Y is selected from OH, cyano, pyrrolyl, pyrrolidinyl, methylpyrrolidinyl, pipecolinyl, imidazolyl, pyrazolyl, pyrazolinyl, pyrazolidinyl, oxazolyl, oxazolidinyl, isooxazolyl, isoozazolidinyl, imidazolidinyl, piperidinyl, piperazinyl, morpholinyl, $O(CH_2)_3N(CH_3)_2$ or ($C_5$–$C_{10}$ alkoxy) or phenyl; or
$X^2$ is S and
$R^8$ is $C_5$–$C_{10}$ alkyl, or $C_nH_{2n}Y$ wherein n=1,2,3 or 4 and Y is selected from OH, phenyl, cyano, pyrrolyl, pyrrolidinyl, methylpyrrolidinyl, pipecolinyl, imidazolyl, pyrazolyl, pyrazolinyl, pyrazolidinyl, oxazolyl, oxazolidinyl, isooxazolyl, isooxazolidinyl, imidazolidinyl, piperidinyl, piperazinyl, morpholinyl, $O(CH_2)_3N(CH_3)_2$ or ($C_5$–$C_{10}$ alkoxy); and
$R^9$ and $R^{10}$ are hydrogen or form an isopropylidene group. Selective removal of the protecting group at the 3,5-position is achieved by the general procedure described in Example 6 to yield partially blocked compounds of formula III where $R^9$ and $R^{10}$ are hydrogen. Preferred compounds of formula III are:

1,2-O-Isopropylidene-6-O-heptyl-α-D-glucofuranose (IIIa);

1,2-O-Isopropylidene-6-O-nonyl-α-D-glucofuranose (IIIb);

1,2-O-Isopropylidene-6-O-dodecyl-α-D-glucofuranose (IIIc);

1,2-O-Isopropylidene-6-O-pentadecyl-α-D-glucofuranose (IIId);

1,2-O-Isopropylidene-6-O-3'-(phenylpropyl)-α-D-glucofuranose (IIIe);

1,2-O-Isopropylidene-6-O-3'-(N',N'-dimethylamino-n-propyl)-α-D-glucofuranose (IIIf);

1,2:3,5-Di-O-isopropylidene-6-O-methoxyoctyl-α-D-glucofuranose (IIIg);

1,2-O-Isopropylidene-6-O-propionitrile-α-D-glucofuranose (IIIh);

1,2:3,5-Di-O-Isopropylidene-6-deoxy-6-amino-(2'-aminoethyl-2''-(N'-methylpyrrolidyl)-α-D-glucofuranose (IIIi);

1,2:3,5-Di-O-Isopropylidene-6-deoxy-6-amino-3'-(phenylpropyl)-α-D-glucofuranose (IIIj);

1,2:3,5-Di-O-Isopropylidene-6-deoxy-6-N-(N'-propyl-pipecolinyl)-α-D-glucofuranose (IIIk);

1,2:3,5-Di-O-Isopropylidene-6-deoxy-6-amino-ethoxyethanol-α-D-glucofuranose (IIIl);

1,2-O-Isopropylidene-6-deoxy-6-amino-3'-(propan-1'-ol)-α-D-glucofuranose (IIIm);

1,2:3,5-Di-O-Isopropylidene-6-deoxy-6-thio-n-heptyl-β-D-glucofuranose (IIIn);

1,2-O-Isopropylidene-6-deoxy-6-thio-n-heptyl-α-D-glucofuranose (IIIo);

1,2:3,5-Di-O-Isopropylidene-6-deoxy-6-thio-2'-(ethyl-N''-pyrrolidyl)-α-D-glucofuranose (IIIp);

1,2-O-Isopropylidene-6-deoxy-6-thio-2'-(ethylpyrrolidyl)-α-D-glucofuranose (IIIq);

1,2:3,5-Di-O-Isopropylidene-6-deoxy-6-thio-3'-(N',N'-dimethylamino-isobutyl)-α-D-glucofuranose (IIIr);

1,2:3,5-Di-O-Isopropylidene-6-deoxy-6-thio-3'-(propan-1'-ol)-α-D-glucofuranose (IIIs); and 1,2-O-Isopropylidene-6-deoxy-6-thio-3'-(phenylpropyl)-α-D-glucofuranose (IIIt).

Synthetic procedures for representative compounds according to this embodiment are shown in the Examples which follow. The activity of selected compounds is shown in Example 17.

EXAMPLE 13

Preparation of
1,2:3,5-di-O-isopropylidene-6-deoxy-6-thio-n-heptyl-α-D-glucofuranose and
1,2-O-Isopropylidene-6-deoxy-6-thio-n-heptyl-α-D-glucofuranose, (IIIo).

Step 1:

The preparation of 1,2:3,5-di-O-isopropylidene-6-deoxy-6-thio-α-D-glucofuranose has been described in U.S. Pat. No. 4,996,195, the disclosure of which is incorporated by reference.

Step 2: The preparation of 1,2:3,5-di-O-isopropylidene-6-deoxy-6-thio-n-heptyl-α,D-glucofuranose:

A mixture of 1,2:3,5-di-O-isopropylidene-6-deoxy-6-thio-α-D-glucofuranose (2.76 g; 0.01 mol) and dry, powder sodium hydroxide (1.20 g) were mixed together and heated at 90°-95° C., in an oil bath, under diminished pressure (0.1 mm Hg). When the formation of water bubbles in the flask ceased (40 minutes), the vacuum line was disconnected and 1-bromoheptane (2.15 g, 0.012 mol) was added. The mixture was heated at the same temperature for 45 minutes (the progress of the reaction as followed by TLC) and then the flask was cooled to ambient temperature. Dichloromethane (75 mL) was added and stirred well. The resultant mixture was filtered and the residue was washed with 75mL more dichloromethane in small portions. The solvent was removed and the residue was purified by flash chromatography using ether:hexane=30:70. The yield of the pure compound was 3.33 g (89.2%). NMR (CDCl$_3$): δ6.01 (d, 1H, H$_1$), 4.59 (d, 1H, H$_2$), 1.34 (m, 12H) 0.89 (t, 3H, CH$_2$CH$_3$). CIMS: 375 (M+1).

Step 3:

One gram of 1,2:3,5-di-O-isopropylidene-6-deoxy-6-thio-n-heptyl-α-D-glucofuranose was dissolved in tetrahydrofuran (1 ml) and hydrochloric acid (3M, 1 mL) was dropwise-added, over a period of 10 minutes, at 0°-10° C. The reaction mixture was stirred at the same temperature for 1.5 hours, and then neutralized with saturated potassium carbonate solution to pH=9.0. The mixture was extracted with ethylacetate (100 mL) and the solvent removed using a rotary evaporator. Evaporation of the solvent gave the crude product which was purified by flash chromatography using Et$_2$O:hexane=60:40. The yield of the pure compound was 0.77 g (86.2%). NMR (CDCl$_3$): δ 5.96 (d, 1H, H$_1$), 4.54 (d, 1H, H$_2$). 0.87 (t, 3H, CH$_2$CH$_3$). CIMS: 335 (M+1), 277 (M−C$_4$H$_9$).

EXAMPLE 14

Preparation of
1,2:3,5-Di-O-Isopropylidene-6-O-n-nonyl-α-D-glucofuranose and
1,2-O-Isopropylidene-6-O-n-nonyl-α-D-glucofuranose, (IIIb).

Step 1: 1,2:3,5-Di-o-Isopropylidene-6-O-n-nonyl-α-D-glucofuranose (R$^8$=C$_9$H$_{18}$).

The synthesis of 1,2:3,5-Di-O-isopropylidene-α-D-glucofuranose (as described in U.S. Pat. No. 4,996,195) was achieved by reacting pivaloyl chloride with 1,2-O-isopropylidene-α-D-glucofuranose at the 6-position, followed by cyclization of 3 and 5-positions with dimethoxypropane and finally hydrolysis of 6-pivaloyl ester. This compound was treated with dry powdered sodium hydroxide and nonylbromide by exactly the same procedure as described in Example 7, step 1.

Step 2: Hydrolysis according to the general procedure described in Example 6 gave the partially blocked compound 1,2-O-Isopropylidene-6-O-n-nonyl-α-D-glucofuranose, (IIIb).

EXAMPLE 15

Preparation of
1,2:3,5-Di-O-isopropylidene-6-deoxy-6-amino-α-D-glucofuranose and
1,2-O-isopropylidene-6-deoxy-6-amino-α-D-glucofuranose.

Step 1: Preparation of 1,2:3,5-Di-O-isopropylidene-6-deoxy-6-amino-α-D-glucofuranose.

A mixture of 1,2:3,5-Di-O-isopropylidene-6-tosyl-α-D-glucofuranose (prepared as described in U.S. Pat. No. 4,996,195) (10 g) and sodium azide (2.5 equivalents) in dry dimethylformamide (100 ml) was heated at 80°-90° C. for 2 hours. The progress of the reaction was monitored by TLC and GC. After the completion of the reaction, the DMF was removed under diminished pressure. The residue was dissolved in ether (150 ml), washed with water (1×50 ml), sodium bicarbonate solution (1×50 ml), the organic layer dried (MGSO$_4$) and the solvent removed. The product 1,2:3,5-di-O-isopropylidene-6-deoxy-6-azido-α-D-glucofuranose so formed was found to be >98% pure by GC, TLC and NMR. 1,2:3,5-di-O-isopropylidene-6-deoxy-6-azido-α-D-glucofuranose was then reduced catalytically with hydrogen using Pd/C by a procedure analgous to that described in Example 9, Step 2. The yield of the pure product, 1,2:3,5-di-O-isopropylidene-6-deoxy-6-amino-α-D-glucofuranose was 96%.

Step 2: Hydrolysis according to the general procedure described in Example 6 gave the partially blocked compound 1,2-O-isopropylidene-6-deoxy-6-amino-α-D-glucofuranose.

EXAMPLE 16

The general procedure for the preparation of 6-deoxy-6-amino or 6-amino substituted glucofuranose was to react 1,2:3,5-di-O-isopropylidene-6-tosyl-α-D-glucofuranose with an appropriately substituted amine (2.2 equivalents), for example 3-phenyl-1-propylamine (IIIJ), at 80°-900C. for 2-3 hours. The progress of the reaction was followed by TLC and GC. After the completion of the reaction, the product was dissolved in ethylacetate (100 ml), washed with a saturated solution of sodium bicarbonate (2×20 ml), brine (1×20 ml), dried (MGSO$_4$) and solvent removed. The 1,2:3,5-Di-O-isopropylidene-6-deoxy-6-amino-3'-(phenylpropyl)-α-D-glucofuranose was then purified by flash chromatography using the appropriate solvent system.

Step 2: Hydrolysis according to the general procedure described in Example 6 gave the partially blocked compound 1,2-O-Isopropylidene-6-deoxy-6-amino-3'-(phenylpropyl) -α-D-glucofuranose.

EXAMPLE 17

Pharmacological Activity of Compounds of Formula III

Compounds of formula III were tested for immunomodulatory and anti-proliferative effects. Results of these studies are described in the data tables below.

Compounds (IIIe), (IIIi), (IIIn) and (IIIp) were found to inhibit the mouse spleen cell blastogenic response in a dose dependent manner, with strong antiproliferative effect (greater than −50% of control) with all compounds tested (Table XV).

A specific example of the inhibitory effects on the ConA mediated blastogenic response of mouse T lymphocytes is given in Table XVI. Compound (IIIp) significantly decreased the proliferative response of splenic T lymphocytes at concentrations ranging from 10 to 750 ug/ml. Additional immunomodulatory effects of the compounds of the present invention were observed in MLR cultures (Table XVII) where compounds (IIId), (IIIe) and (IIIi) were demonstrated to exert strong non dose dependent inhibition of T lymphocyte proliferation. Compound (IIId) was found to exhibit strong inhibitory effects on the MLR at concentrations ranging from 10 to 300 uM whereas compounds (IIIe) and (IIId) were active at the highest dose levels only.

Results of the testing of compounds of the present invention for modulatory effects on mouse peritoneal macrophage production are presented in Table XVIII. IL-1 activity was demonstrated to be significantly lowered in cultures containing 2.5, 10, and 100 ug/ml of compound (IIIi). Compound (IIIE) was significantly inhibitory to IL-1 activity at 2.5, 10, 25 and 100 ug/ml. Both compounds appeared to exert inhibitory effects on IL-1 activity in non dose dependent manner.

TABLE XVII

| Compound | Concentration of Invention (um) | Mean O.D. Allogenic | Mean O.D. Syngeneic | % Change From b Control |
|---|---|---|---|---|
| Group A | | | | |
| Vehicle Control A | | 0.245 | 0.075 | |
| (IIIe) | 3 | 0.174 | 0.052 | −19 |
| | 10 | 0.122 | 0.081 | −73 |
| | 30 | 0.084 | 0.066 | −88 |
| | 100 | 0.034 | 0.024 | −93 |
| | 300 | 0.009 | 0.010 | −101 |
| (IIIi) | 3 | 0.128 | 0.090 | −15 |
| | 10 | 0.180 | 0.102 | −48 |
| | 30 | 0.165 | 0.078 | −42 |
| | 100 | 0.095 | 0.066 | −81 |
| | 300 | 0.019 | 0.030 | −107 |
| Group B | | | | |
| Vehicle Control B | | 0.182 | 0.099 | |
| (IIId) | 3 | 0.210 | 0.138 | −13 |
| | 10 | 0.197 | 0.128 | −17 |
| | 30 | 0.104 | 0.032 | −13 |
| | 100 | 0.021 | 0.019 | −98 |

TABLE XV

EFFECT OF THE INVENTION ON THE CON-A RESPONSE OF NORMAL SPLEEN CELLS[a]

| Compound | Concentration of Con-A (ugg/ml) | % Change from Control[b] Concentration of Invention (ug/ml) | | | | | | |
|---|---|---|---|---|---|---|---|---|
| | | 750 | 300 | 100 | 25 | 10 | 2.5 | 1 |
| (IIIp) | 4 | −91 | −91 | −55 | −33 | −40 | NT | −17 |
| | 1 | −94 | −63 | −11 | +40 | −23 | NT | −65 |
| (IIIi) | 4 | NT | NT | −95 | −50 | −9 | −14 | −9 |
| | 1 | NT | NT | −91 | −23 | 10 | 16 | 25 |
| (IIIe) | 4 | NT | NT | −100 | −99 | −97 | −91 | −76 |
| | 1 | NT | NT | −99 | −99 | −98 | −94 | −78 |
| (IIIn) | 4 | −98 | −99 | −76 | −16 | −12 | NT | 1 |
| | 1 | −99 | −99 | −84 | −27 | −29 | NT | −4 |
| CSP | 4 | NT | NT | −92 | −66 | −57 | −34 | −26 |
| | 1 | NT | NT | −92 | −78 | −50 | −61 | −16 |
| AZT | 4 | NT | NT | −100 | −99 | −99 | −99 | −97 |
| | 1 | NT | NT | −99 | −99 | −99 | −98 | −96 |

[a]Experimental compounds, cyclosporin (CSP) or AZT were suspended in DMSO (vehicle) diluted into medium. Normal spleen cells were cultured with 4 or 1 ugg/ml Con-A together with various doses of experimental compound. The control contained medium with vehicle only. The effect of these compounds on the blastogenic response of spleen cells was determined by pulsing the cells with $^3$H-thymidine after 48 hours of culture and harvesting the culture 18 hours thereafter.
[b]Results are expressed as percent change from the response of spleen cells cultured with control. NT = not tested.

TABLE XVI

EFFECT OF EXPERIMENTAL COMPOUNDS ON THE CON-A RESPONSE OF NORMAL SPLEEN CELLS[a]

| Compound | Con-A | Blastogenic response of normal spleen cells to Con-A; % effect | | | | | |
|---|---|---|---|---|---|---|---|
| control | 4 ug/ml | 97,141 ± 5,802 | | | | | |
| | 1 ug/ml | 72,234 ± 6,650 | | | | | |
| | | Dose of experimental compound added to blastogenesis assay: | | | | | |
| | | 750 ug/ml | 300 ug/ml | 100 ug/ml | 25 ug/ml | 10 ug/ml | 1 ug/ml |
| (IIIp) | 4 ug/ml | 8,402 ± 3,070 −91** | 8,310 ± 945 −91** | 43,864 ± 9,618 −55# | 65,424 ± 13,480 −33* | 58,381 ± 7,921 −40# | 81,109 ± 15,059 −17 |
| | 1 ug/ml | 3,976 ± 1,922 −94** | 26,948 ± 13,540 −63** | 64,122 ± 7,847 −11# | 101,268 ± 23,586 −40* | 55,282 ± 17,762 −23 | 118,909 ± 28,302 65 |

[a]Experimental compounds were first suspended in DMSO or ethanol, then diluted into medium and added at various concentrations to normal spleen cells and either 4 or 1 ug/ml Con-A. Control cultures contained comparable concentrations of DMSO or ethanol. The effect of these compounds on the blastogenic response of the spleen cells was assessed by pulsing the cells with $^3$H-thymidine after 48 hours of culture and harvesting the spleen cells 18 hours thereafter. Data are expres sed as cpm of triplicates ± SD.
[b]The effect of experimental compounds on the blastogenic response of normal splenic T-lymphocytes is expressed as percent change from the response of spleen cells cultured in the absence of experimental compounds. Significance of the effect of experimental compounds: *, $P < 0.05$; #, $P < 0.01$; **, $P < 0.001$.

TABLE XVII-continued

| Compound | Concentration of Invention (um) | Mean O.D. Allogenic | Mean O.D. Syngeneic | % Change From b Control |
|---|---|---|---|---|
| | 300 | 0.015 | 0.021 | −107 |

[a]Experimental compounds were suspended in DMSO, diluted in medium and added at the indicated concentrations to mouse spleen cells mixed lymphocyte cultures. Vehicle control cultures contained medium plus the assay concentration of DMSO. The effect of the experimental compounds on the spleened T cell proliferative responses to both allogeneic and syngeneic (background proliferation) stimulators. T cell proliferative responses were determined after 5 days of culture by MTT reduction analysis with mean optical density (O.D.) corresponding to the amount of cellular proliferation in triplicate wells.
[b]Results are expressed as percentage change from the T cell proliferative response in vehicle control cultures.

TABLE XVIII

EFFECT OF COMPOUNDS ON THE PRODUCTION OF INTERLEUKIN-1 BY PERITONEAL MACROPHAGES

| Addition to thymocytes | $^3$H-Thymidine uptake by thymocytes; % effect | | | | | | | |
|---|---|---|---|---|---|---|---|---|
| | 0.375% | 0.094% | 0.0375% | $9 \times 3 \times 10^3$% | $3.75 \times 10^3$% | $3.75 \times 10^{-4}$% | $3.75 \times 10^{-5}$% | $3.75 \times 10^{-6}$% |
| DMSO-PEC sup. | 6,739 ± 397 | 7,662 ± 798 | 7,679 ± 402 | 8,345 ± 617 | 7,086 ± 625 | 7,720 ± 886 | 8,223 ± 483 | 8,202 ± 206 |

| | Dose of experimental compound added to PEC cultures or control medium culture | | | | | | | |
|---|---|---|---|---|---|---|---|---|
| | 100 ug/ml | 25 ug/ml | 10 ug/ml | 2.5 ug/ml | 1 ug/ml | 0.1 ug/ml | 0.01 ug/ml | 0.001 ug/ml |
| (IIIi) PEC sup. | 2,328 ± 278 (−65)*[b] | 5,052 ± 140 (−34) | 5,169 ± 870 (−33)* | 5,382 ± 45 (−35)* | 9,561 ± 113 (+22)* | 10,740 ± 724 (+39)* | 9,902 ± 888 (+20)* | 11,367 ± 906 (+39)* |
| (IIIe) PEC sup. | 1,129 ± 299 (−83)* | 1,840 ± 301 (−76)* | 2,586 ± 553 (−66)* | 3,676 ± 506 (−56)* | 4,279 ± 691 (+45)* | 8,049 ± 282 (+4)* | 8,908 ± 773 (+8)* | 7,276 ± 399 (+11)* |

Experimental compounds, cyclosporin (CSP) or AZT were suspended in DMSO and diluted into medium. They were then added to peritoneal exudate cells (PEC) together with 10 ug/ml LPS. After 24 hr. culture supernatants were collected and added for the subsequent 48 hr. to thymocytes and 1 ug/ml PHA. Thymocytes are used as indicators for IL-1 which selectively stimilates their growth. The effect of these compounds on thymocytes was measured by pulsing the cells with $^3$H-thymidine and harvesting the cells 18 hours thereafter. Data shown is mean cpm of triplicates ± SD. Shown in parenthesis is the percent effect of adding drug to PEC when compared to effect of PEC cultured without drug.
[b]Significance of the effect of drug: *, $P < 0.001$; *P $< 0.01$; *, $P < 0.05$.

The compounds of the present invention also include the following monosaccharides:

(3S) 1,2-O-isopropylidene-α-D-ribo-hexos-3-ulose-1,4:3,6-difuranose; and

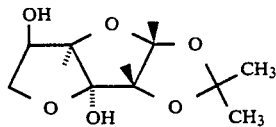

(IV)

Methyl 3-O-3'-(N',N'-dimethylamino-n-propyl)-6-deoxy-D-glucopyranoside.

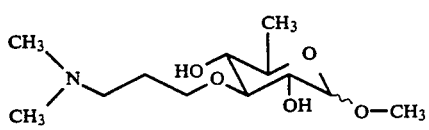

(V)

EXAMPLE 18

Preparation of
1,2-O-Isopropylidene-α-D-ribo-hexos-3-ulose-1,4:3,6-difuranose, (IV).

Two grams of 1,2:5,6-di-O-isopropylidene-α-D-ribohexofuranos-3-ulose were dissolved in tetrahydrofuran (2mL) and cooled to 0°–50° C. Aqueous perchloric acid (2mL, 30%) was added dropwise with stirring over a period of 10 minutes. The progress of the reaction was monitored by TLC. When the hydrolysis was complete (40 minutes), the solution was neutralized with a saturated solution of potassium carbonate and extracted with ethyl acetate. Removal of the solvent gave a crude product which was purified by medium pressure column chromatography using silica gel "G" (10–40; μ) and eluting with ether:hexane=50:50. The yield of the white crystalline material was 1.48 g (87.6%), m.p. 81°–82° C. IR (KBr): 3390cm$^{-1}$ (broad OH), No>C=O (stretching). $^1$H NMR (CDCl$_3$): δ5.97 (d, 1H), 4.51–4.41 (m, 4H), 4.26 (m, 1H), 3.78 (m, 1H), 3.07 (d, 1H), 1.58 (d, 3H), 1.40 (s, 3H). $^{13}$C NMR (CDCl$_3$, APT): δ113.99, 110.93 (C-3 and C-9), 106.98, 84.04, 82.78, 71.07 (C-1, C-2, C-4, C-5), 73.56 (C-6), 27.22, 27.18 (C-8, C-9). CIMS: 219 (M+1).

EXAMPLE 19

Pharmacological Activity of
1,2-O-Isopropylidene-α-D-ribo-hexos-3-ulose-1,4:3,6-difuranose, (IV).

Compound IV was teated in the Bud-B skin cell fibroblasts assays as described in Example 12. As can been seen from Tables XIX, XX and XXI below, the compounds of the invention produced significant, non dose dependent decreases in the Bud-8 skin cell fibroblast proliferation in those cultures that contained 1, 10, 25 and 100 ug/ml, respectively, when compared to the control cultures that did not contain the compounds of the invention. Cytotoxicity was not observed at these concentrations of the test compound. Cytotoxic effects were observed in the highest concentrations tested (300 ug/ml and 750 ug/ml). These antiproliferative effects correlates with decreases in Bud-8 skin cell fibroblast production of PGE$_2$ and LTB$_4$ (Tables XX and XXI) where significantly decrease of levels of both pro-inflammatory mediators are seen at several non-toxic doses of compound IV.

TABLE XIX

Effect of Compounds IV on the Proliferation of BUD-8 Skin Cells

| Compound | $^3$H-Thymidine uptake by BUD-8 Skin cells, % effect | | | | | |
|---|---|---|---|---|---|---|
| None | 7,305 ± 492 | | | | | |
| | Dose of experimental compound added to BUD-8 cells: | | | | | |
| | 750 ug/ml | 300 ug/ml | 100 ug/ml | 25 ug/ml | 10 ug/ml | 1 ug/ml |

TABLE XIX-continued

Effect of Compounds IV on the Proliferation of BUD-8 Skin Cells

| Compound | | | | | | |
|---|---|---|---|---|---|---|
| IV | 2,658 ± 247 <br> −64c | 2,882 ± 387 <br> −61c | 4,032 ± 3 <br> −45 | 3,791 ± 451 <br> −48 | 4,077 ± 374 <br> −44 | 3,607 ± 87 <br> −51 |
| Indo. | 6,043 ± 184 <br> −17* | | | | | |
| NDGA | 6,925 ± 313 <br> −5 | | | | | |

<sup>a</sup>Experimental compounds were first suspended and diluted in medium, then added at various concentrations to human BUD-8 skin cell fibroblasts. The effect of these compounds on the proliferation of the BUD-8 skin cells was assessed by pulsing the cells with $^3$H-thymidine after 72 hours of culture and harvesting the BUD-8 cells 18 hours thereafter. Data are expressed as cpm of triplicates ± SD.
<sup>b</sup>The effect of experimental compounds on the proliferation of BUD-8 cells is expressed as percent change from the amount of $^3$H-thymidine incorporated in the absence of experimental compounds. Significance of the effect of experimental compounds: *, $P < 0.05$; #, $P < 0.01$, **, $P < 0.00$.
<sup>c</sup>Evidence of toxicity of compound on BUD-8 cells on the basis of either cell rounding or granularity.
A simultaneous decrease in levels of PGE$_2$ and LTB$_4$, as quantified in the cell culture medium was also seen in Table XX and Table XXI.

TABLE XX

Effect of Compound IV PGE$_2$ Production by BUD-8 Skin Cells

| Compound | pg PGE$_2$/50 ul supernatant (PGE$_2$ production/10$^5$ BUD-8 cells); % effect | | | | | |
|---|---|---|---|---|---|---|
| None | 15.9 ± 3.5 (1,033) | | | | | |
| | Dose of experimental compound added to BUD-8 cells: | | | | | |
| | 750 ug/ml | 300 ug/ml | 100 ug/ml | 25 ug/ml | 10 ug/ml | 1 ug/ml |
| IV | 4.0 ± 0.5 (82) <br> −65#c | 23.7 ± 1.5 (1654) <br> −67#c | 13.6 ± 4.4 (*850) <br> −59# | 7.6 ± 0.6.7 (366) <br> −52* | 7.5 ± 0.9 (362) <br> −52* | 7.1 ± 1.0 (336) <br> −51* |
| Indo. | 5.3 ± 0.5 (187) <br> −66# | | | | | |
| NDGA | 14.7 ± 0.8 (933) <br> −8 | | | | | |

<sup>a</sup>Experimental compounds were diluted into medium and then added at various concentrations to human BUD-8 skin cell fibroblasts. The effect of these compounds on their PGE production was assessed by radioimmunoassay. All values are the results of triplicate determinations. Data are expressed as pg PGE$_2$ in 50 ul supernatant ± SD. In parentheses is the calculated pg PGE$_2$ production per 10$^5$ cells.
<sup>b</sup>The effect of experimental compounds on the amount of PGE$_2$ in the supernatants of BUD-8 skin cells is expressed as percent change from the amount of PGE$_2$ of cells cultured in the absence of experimental compounds. Significance of the effect of experimental compounds: *, $P < 0.05$; #, $P < 0.01$, **, $P < 0.001$.
<sup>c</sup>Evidence of toxicity of compound on BUD-8 cells on the basis of either cell rounding or granularity.

TABLE XXI

Effect of Compound IV on LTB$_4$/Production by BUD-8 Skin Cells

| Drug | pg LTB$_4$100 ul supernatant (LTB$_4$ production/10$^5$ BUD-8 cells); % effect | | | | | |
|---|---|---|---|---|---|---|
| None | 35.8 ± 2.0 (1,591) | | | | | |
| | Dose of experimental compound added to BUD-8 cells: | | | | | |
| | 750 ug/ml | 300 ug/ml | 100 ug/ml | 25 ug/ml | 10 ug/ml | 1 ug/ml |
| Ex. 2 | 23.5 ± 0.2 (973) <br> −35c | 25.7 ± 5.0 (1,083) <br> −28c | 17.3 ± 0.9 (665) <br> −52 | 17.7 ± 3.8 (683) <br> −51# | 19.9 ± 3.8 (794) <br> −45# | 36.4 ± 5.2 (1,621) <br> +2 |
| Indo. | 39.4 ± 5.3 (1,771) <br> +10 | | | | | |
| NDGA | 19.9 ± 1.5 (794) <br> −45** | | | | | |

<sup>a</sup>Experimental compounds were diluted directly into medium and then added at various concentrations to human BUD-8 skin cell fibroblasts. The effect of these compounds on their LTB$_4$ production was assessed by radioimmunoassay. All values are the results of triplicate determinations. Data are expressed as pg LTB$_4$ in 100 ul supernatant ± SD. In parentheses is the calculated pg LTB$_4$ secretes per 10$^5$ cells.
<sup>b</sup>The effect of experimental compounds on the amount of LTB$_4$ in the supernatants of BUD-8 skin cells is expressed as per cent change from the amount of LTB$_4$ of cells cultured in the absence of experimental compounds. Significance of the effect of experimental compounds: *, $P < 0.01$; **, $P < 0.001$.
<sup>c</sup>Evidence of toxicity of compound on BUD-8 cells on the basis of either cell rounding or granularity.

EXAMPLE 20

Preparation of Methyl 3-O-3'-(N',N'-dimethylamino-n-propyl)-6-deoxy-D-glucopyranoside (V).

Step 1: The preparation of 1,2-O-isopropylidene-3-O-3'-(N',N'-dimethylaminopropyl)-6-O-p-toluenesulfonyl-α-D-glucofuranose, (1).

Ten grams of 1,2-O-isopropylidene-3-O-3'-(N',N'-dimethylaminopropyl)-α-D-glucofuranose were dissolved in 30 mL of anhydrous pyridine and cooled to 5° C. in an ice-water bath. p-Toluenesulfonyl chloride (6.25 g, 1 eq), dissolved in 20 mL of pyridine, was added to the stirred solution over a period of 30 minutes. The reaction was then allowed to attain ambient temperature over a period of 1 hour. After a total reaction time of 3 hours, the solvents were removed under vacuum, and the residue was dissolved in dichloromethane (200 mL), and the organic phase washed with 25 mL of saturated sodium hydrogen carbonate solution. The combined organic phase was washed with water and brine, dried over anhydrous magnesium sulfate and evaporated to give 14.3 g (95%) of the tosylate as a glassy material, that solidified on trituration with ether. CIMS: 460 (M+1)

Step 2: The preparation of 1,2-O-isopropylidene-6-deoxy-3-O-3'-(N',N'-dimethylaminopropyl)-α-D-glucofuranose, (2).

Ten grams of 1,2-O-Isopropylidene-3-O-3'-(N',N'-dimethylaminopropyl)-6-O-p-toluenesulfonyl-α-D-glucofuranose (1) were dissolved in 60 ml of freshly distilled tetrahydrofuran and the mixture was gradually added to a stirred suspension of 1.7 g (2 eq) of lithium aluminum hydride in 50 mL of THF. After the addition was complete, the mixture was refluxed for 2 hours. It was then cooled in an ice bath and the excess lithium aluminum hydride was quenched by the addition of 2 ml of water, followed by 5 ml of 15% sodium hydroxide solution. The mixture was filtered through Celite and the filtrate was evaporated to give 5.91 g (94%) of the 1,2-O-isopropylidene-6-deoxy-3-O-3'-(N',N'dimethylaminopropyl)-α-D-glucofuranose (2) product which was used without purification for the next step. CIMS: 290 (M+1) NMR (CDCl$_3$): δ5.92 (d, 1H, H$_1$), 4.55 (d, 1H, H$_2$), 3.95 (m, 2H, H$_3$ and H$_4$), 3.83 (m, 1H, H$_5$), 3.48 (m, 2H, OCH$_2$), 2.28 (s, 3H, CH$_3$), 1.48 and 1.32 (s, 3H each, C(CH$_3$)$_2$).

Step 3: The preparation of 6-Deoxy-3-O-3'-(N',N'-dimethylaminopropyl)-D-glucopyranose, (3).

Three grams of 1,2-O-isopropylidene-3-O-3'-(N',N'-dimethylaminopropyl)-6-deoxy-α-D-glucofuranose (2) was dissolved in 10 mL of tetrahydrofuran and 5 ml of 3N hydrochloric acid was added. The mixture was stirred for 2 hours at 500° C., cooled and neutralized with 20% sodium hydroxide solution. The solvents were removed under vacuum and the residue was extracted with hot ethyl acetate. The organic phase was dried over magnesium sulfate and evaporated to give 2.2 g (85.4%) of the free sugar. The 6-Deoxy-3-O-3'-(N',N'-dimethylaminopropyl) -D-glucopyranose (3) was used directly for the next step.

Step 4: The preparation of methyl 3-O-3'-(N',N'-dimethylaminopropyl)-6-deoxy-D-glucopyranoside, (V).

The 6-Deoxy-3-O-3'-(N',N'-dimethylaminopropyl)-D-glucopyranose (3) (1.8 g) was dissolved in 10 mL of a methanol containing approximately 5% of anhydrous hydrogen chloride by weight. After 2.5 hours at ambient temperature, the methanol was evaporated, the residue was neutralized with saturated potassium carbonate and extracted several times with dichloromethane. The combined extract was dried over magnesium sulfate and evaporated to give the crude product, which was purified by flash chromatograph (100% ethyl acetate, then 20% methanol in ethyl acetate) to give 1.64 g (86.5%) of the methyl 3-O-3'-(N',N'-dimethylamino-n-propyl)-6-deoxy-D-glucopyranoside compound. The $^1$H NMR showed the presence of a mixture of α and β-isomers in the ratio of 6:4. CIMS: 264 (M+1)

EXAMPLE 21

Pharmacological Activity of Methyl 3-O-3'-(N',N'-dimethylamino-n-propyl)-6-deoxy-D-glucopyranoside, (V).

Methyl 3-O-3'-(N',N'-dimethylamino-n-propyl)-6-deoxy-D-glucopyranoside of this invention has demonstrated inhibitory effects on the proliferation of GS-109-V-20 human skin cell fibroblasts.

A compound that inhibits fibroblast proliferation has the potential to be utilized as a dermatological drug used to treat chronic dermatorse, such as psoriasis and autoimmune disorders which result in joint inflammation, such as rheumatoid arthritis. Also, an anti-proliferative effect may well be observed with other tissues, such as those that line the blood vessels, or joints, the uncontrolled proliferation of which produce disease, thereby broadening the scope of potential applications.

Specific Method: Fibroblast Assay

The effect of methyl 3-O-3'-(N',N'-dimethylamino-n-propyl)-6-deoxy-D-glucopyranoside on the proliferative capacity of human GS-109-V-20 skin fibroblasts was measured with the use of $^3$H-thymidine incorporation assay. Cultured skin cells were detached from the surface of tissue culture flasks mechanically with a Teflon scraper. The cells were washed, resuspended in incubation medium and the viabilities determined. These cells were then plated in triplicate at a density of $1 \times 10^3$ cells/0.1 ml/microtiter well. To these cells was added 0.1 ml incubation medium containing the methyl 3-O-3'-(N',N'-dimethylamino-n-propyl)-6-deoxy-D-glucopyranoside compound.

After 3 days of culture, 1#uCi $^3$H-thymidine was added in 50 ul volume to each culture well of the microtiter plates. Eighteen hours later, each of the GS-109-V-20 cultures was examined morphologically for evidence of drug-induced toxicity such as cell rounding or granularity. The $^3$H-thymidine-pulsed cells were then precipitated and the amount of $^3$H-thymidine incorporation was counted on a liquid scintillation counter.

Methyl 3-O-3'-(N',N'-dimethylamino-n-propyl)-6-deoxy-D-glucopyranoside was suspended directly into the medium by extensive sonication, without being filter-sterilized. A range of doses of this compound was used to measure effects of this compound upon GS-109-V-20 cell proliferation. The following doses were used:

| Group 1: | 0 ug/ml | Group 7: | 10 ug/ml |
|---|---|---|---|
| Group 2: | 0.001 ug/ml | Group 8: | 25 ug/ml |
| Group 3: | 0.01 ug/ml | Group 9: | 100 ug/ml |
| Group 4: | 0.1 ug/ml | Control Groups: | |
| Group 5: | 1 ug/ml | Control: | $2 \times 10^{-6}$ M Indomethacin |
| Group 6: | 2.5 ug/ml | Control: | $2 \times 10^{-6}$ N NDGA |

Specific method: Incubation medium

The incubation medium used for culturing the GS-109-V-20 cells was RPMI-1640 medium containing 10% fetal bovine serum, 100 ug/ml streptomycin, 100 U/ml penicillin, 0.2M Hepes buffer solution, $5 \times 10^{-5}$M 2-mercaptoethanol and 2 Mm glutamine.

Specific method: Human skin cells

The human skin cell fibroblast line, GS-109-V-20, was obtained from the American Type Culture-Collection. This is a fibroblast-like cell line which was originally derived from the skin of an 18 year old Caucasian male with Gardner's syndrome, an autosomal dominant condition which predisposes to carcinoma and multiple polygas of the colon (American Type Culture Collection, Catalogue of Cell Lines and Hybridomas, 6th Ed., 150, 1988). These cells were selected for use because they are considered to exist in an initiated state, as opposed to being normal or transformed, and have a more extensive population doubling time and survival period in culture than do normal fibroblasts. In this regard, they would more closely reflect the biological characteristics of psoriatic or rheumatoid synovial fibroblasts which also proliferate more extensively than do normal fibroblasts, but not as extensively as immortalized transformed tumor cells.

The number of GS-109-V-20 cells was expanded for use in the described assays by culture in 25 cm² flasks at 37° C. in an atmosphere of 5% $CO_2$ in air. At approximately 4–5 day intervals, or when confluence was reached, the cells were passaged. This was accomplished by detaching the cells by trypsinization, washing and reseeding the cells at a lower density into fresh tissue culture flasks.

Statistical analysis of data

The Student's t test was used to determine the significance of the difference between values for skin cells cultured in the presence of experimental compounds versus in control medium alone.

The difference between the proliferative abilities of the skin cells cultured in the presence of methyl 3-O-3'-(N',N'-dimethylamino-n-propyl)-6-deoxy-D-glucopyranoside of the present invention versus that observed with the control cultures, can be seen in the data presented in Table XXII below.

A significant inhibitory effect was observed in a non-dose-dependent manner for cultures receiving the methyl 3-O-3'-(N',N'-dimethylamino-n-propyl)-6-deoxy-D-glucopyranoside. It is important to note that the inhibition occurred to the same degree, irrespective of the concentration employed without evidence of cytotoxicity, and may suggest that this compound exerts these effects through novel mechanisms.

priate, compounds containing an amino functionality may be in the form of an acid-addition salt. Preferred acid addition salts are hydrochloric acid salts.

The present invention also encompasses a method of treating animals or humans suffering from inflammatory and/or autoimmune disorders which comprises administering to an animal or person an effective amount of at least one of the compounds of the invention or an acid-addition salt thereof, with or without a pharmaceutically acceptable carrier. The compositions according to the invention can be administered orally, topically, rectally, internally, or, if desired, parenterally. Oral administration is preferred.

Suitable solid or liquid galenical formulations, for example are granules, powders, coated tablets, microcapsules, suppositories, syrups, elixirs, suspensions, emulsions, drops or injectable solutions. Preparations having a protracted release of the active compound may also be used. These formulations can also contain additives such as excipients, disintegrants, binders, coating agents, swelling agents, glidants, or lubricants, flavors, sweeteners or solubilizers. Frequently used additives are, for example, magnesium carbonate, titanium dioxide, lactose, mannitol and other sugars, talc, lactoalbumin, gelatin, starch, cellulose and its derivatives, animal and vegetable oils, polyethylene glycols, polysorbates and solvents, such as sterile water and monohydric or polyhydric alcohols, i.e. glycerol.

TABLE XXII

Effect of Methyl 3-0-3'-(N',N'-dimethylamino-n-propyl)-6-deoxy-D-glucopyramoside (V) on the Proliferation of GSV-109-V-20 Skin Cell Fibroblasts[a]

| Compound | ³H-Thymidine uptake by GS-109-V-20 skin cells, % effect | | | | | | | |
|---|---|---|---|---|---|---|---|---|
| None | 2,913 ± 261 | | | | | | | |
| | Dose of experimental compound added to GS-109-V-20 fibroblasts: | | | | | | | |
| | 100 ug/ml | 25 ug/ml | 10 ug/ml | 2.5 ug/ml | 1 ug/ml | 0.1 ug/ml | 0.01 ug/ml | 0.001 ug/ml |
| IV | 647 ± 541 | 946 ± 41 | 900 ± 189 | 1,044 ± 106 | 1,237 ± 301 | 1,052 ± 177 | 976 ± 469 | 2,557 ± 258 |
| | −78# | −68** | −69** | −64** | −58** | −64** | −66# | −12 |
| Indo. | 3,317 ± 351 | | | | | | | |
| | −14 | | | | | | | |
| MDGA | 3,179 ± 489 | | | | | | | |

[a]Experimental compounds were suspended and diluted into medium. Human GS-109-V-20 skin cell fibroblasts were cultured with various doses of experimental compounds. The control contained medium alone. The effect of these compounds on the proliferation of the GS-109-V-20 skin cells was assessed by pulsing the cells with ³H-thymidine after 72 hours of culture and harvesting the GS-109-V-20 cells 18 hours thereafter. Data are expressed as cpm of triplicates ± SD.
The effect of experimental compounds on the proliferation of GS-109-V-20 cells is expressed as per cent change from the amount of ³H-thymidine incorporated in the presence of control. Significance of the effect of experimental compounds: *, $P < 0.05$; #, $P < 0.01$, **, $P < 0.001$.

The compounds of the present invention as shown by formulae I, II, III, IV and V are useful for treating mammals with inflammatory and/or autoimmune disorders such as psoriasis, atopic dermatitis, rheumatoid arthritis, ostearthritis, scleroderma and systemic lupus erythematosus. The proliferative activities of these compounds broaden the potential scope of their application as therapeutic agents for the treatment of uncontrolled proliferation of particular cell types. Due to their valuable pharmacological properties, the compounds of the present invention or their physiologically acceptable salts are particularly suitable for use as active compounds in pharmaceutical compositions for the treatment of, for example, chronic inflammatory rheumatic disorders.

The compounds can either be administered alone in the form of microcapsules, in mixtures with one another or in combination with acceptable pharmaceutical carriers. The invention, thus, also relates to pharmaceutical compositions which comprise an effective amount of at least one compound of the present invention with or without a pharmaceutically acceptable carrier. If appro- The pharmaceutical compositions are preferably produced and administered in dosage units, each unit containing as active component a certain dose of at least one compound of the present invention and/or at least one of its physiologically acceptable acid-addition salts. The dose can range from about 1 to 100 mg per kilogram of body weight per day, preferably 10–200 mg. In the case of in vitro testing, the effective amount to achieve a 50% inhibition of the cultured cells range from about 1–200 ug/ml of culture medium, preferably 10–100 ug/ml.

The claimed invention is:
1. A compound of formula III:

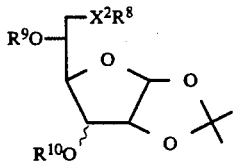

(III)

wherein:

$X^2$ is O, $R^9$ and $R^{10}$ are hydrogen or form an isopropylidene group, $R^8$ is $C_8$–$C_{20}$ alkyl, or $C_nH_{2n}Y$, wherein n=1,2,3 or 4 and Y is selected from phenyl, cyano, pyrrolyl, methylpyrrolidinyl, pipecolinyl, imidazolyl, pyrazolyl, pyrazolinyl, pyrazolidinyl, oxazolyl, oxazolidinyl, isooxazolyl, isooxazolidinyl, imidazolidinyl, piperidinyl, piperazinyl, morpholinyl, $O(CH_2)_3N(CH_3)_2$, ($C_5$–$C_{10}$ alkoxy), $NH_2$ and $N(CH_3)_2$; or $X^2$ is NH, $R^9$ and $R^{10}$ are hydrogen or form an isopropylidene group, and $R^8$ is $C_nH_{2n}Y$, wherein n=1,2,3 or 4 and Y is selected from OH, cyano, pyrrolyl, pyrrolidinyl, (N-methylpyrrolidinyl)amino, methylpyrrolidinyl, pipecolinyl, imidazolyl, pyrazolyl, pyrazolinyl, pyrazolidinyl, oxazolyl, oxazolyl, oxazolidinyl, isooxazolyl, isoozazolidinyl, imidazolidinyl, piperidinyl, piperazinyl, morpholinyl, $O(CH_2)_3N(CH_3)_2$, ($C_5$–$C_{10}$ alkoxy) and with the exception of the compound wherein $R^9$ and $R^{10}$ are hydrogen and $R^8$ is $C_nH_{2n}Y$, wherein n=1 and Y is phenyl; or $X^2$ is S, $R^9$ and $R^{10}$ are hydrogen or form an isopropylidene group, and $R^8$ is $C_5$–$C_{10}$ alkyl or $C_nH_{2n}Y$ wherein n=1,2,3 or 4 and Y is selected from OH, phenyl, cyano, pyrrolyl, pyrrolidinyl, methylpyrrolidinyl, pipecolinyl, imidazolyl, pyrazolyl, pyrazolinyl, pyrazolidinyl, oxazolyl, oxazolidinyl, isooxazolyl, isooxazolidinyl, imidazolidinyl, piperidinyl, piperazinyl, morpholinyl, $CH(CH_3)CH_2N(CH_3)_2$, $O(CH_2)_3N(CH_3)_2$ or ($C_5$–$C_{10}$ alkoxy), with the exception of the compound wherein $R^9$ and $R^{10}$ are hydrogen and $R^8$ is $C_nH_{2n}Y$, wherein n=1 and Y is phenyl.

2. The compound according to claim 1, wherein said compound is an allofuranose.

3. The compound according to claim 1, wherein $X^2$ is O, $R^9$ and $R^{10}$ are hydrogen or form an isopropylidene group, and $R^8$ is selected from heptyl, nonyl, dodecyl, pentadecyl, 3'-(phenylpropyl), 3'-(N',N'-dimethylamino-n-propyl), methoxyoctyl and propionitrile.

4. A compound according to claim 1, wherein $X^2$ is NH, $R^9$ and $R^{10}$ are hydrogen or form an isopropylidene group, and $R^8$ is selected from 2'-aminoethyl-2''-(N'-methylpyrrolidyl), 3'-(phenylpropyl), N'-propylpipecolinyl, ethoxyethanol, and 3'-(propan-1'-ol).

5. A compound according to claim 1, wherein $X^2$ is S, $R^9$ and $R^{10}$ are hydrogen or form an isopropylidene group, and $R^8$ is selected from n-heptyl, 2'-(ethylpyrrolidyl), 3'-(N',N'-dimethyl-amino-isobutyl, 3'-(propan-1'-ol), and 3'-(phenylpropyl).

6. A compound according to claim 1, wherein said compound is a glucofuranose.

7. A compound according to claim 6, wherein said compound is selected from:
1,2-O-Isopropylidene-6-O-heptyl-α-D-glucofuranose;
1,2-O-Isopropylidene-6-O-nonyl-α-D-glucofuranose;
1,2-O-Isopropylidene-6-O-dodecyl-α-D-glucofuranose;
1,2-O-Isopropylidene-6-O-pentadecyl-α-D-glucofuranose;
1,2-O-Isopropylidene-6-O-3'-(phenylpropyl)-α-D-glucofuranose;
1,2-O-Isopropylidene-6-O-3'-(N',N'-dimethylamino-n-propyl)-α-D-glucofuranose;
1,2:3,5-Di-O-isopropylidene-6-O-methoxyoctyl-α-D-glucofuranose;
1,2-O-Isopropylidene-6-O-propionitrile-α-D-glucofuranose;
1,2:3,5-Di-O-Isopropylidene-6-deoxy-6-amino-[2'-aminoethyl-2''-(N'-methylpyrrolidyl)]-α-D-glucofuranose;
1,2:3,5-Di-O-Isopropylidene-6-deoxy-6-amino-3'-(phenylpropyl)-α-D-glucofuranose;
1,2:3,5-Di-O-Isopropylidene-6-deoxy-6-N-(N'-propylpipecolinyl)-α-D-glucofuranose;
1,2:3,5-Di-O-Isopropylidene-6-deoxy-6-amino-ethoxyethanol-αD-glucofuranose;
1,2-O-Isopropylidene-6-deoxy-6-amino-3'-(propan-1'-ol)-α-D-glucofuranose;
1,2:3,5-Di-O-Isopropylidene-6-deoxy-6-thio-n-heptyl-α-D-glucofuranose;
1,2-O-Isopropylidene-6-deoxy-6-thio-n-heptyl-α-D-glucofuranose;
1,2:3,5-Di-O-Isopropylidene-6-deoxy-6-thio-2'-(ethylpyrrolidyl)-α-D-glucofuranose;
1,2-O-Isopropylidene-6-deoxy-6-thio-2'-(ethylpyrrolidyl)-α-D-glucofuranose;
1,2:3,5-Di-O-Isopropylidene-6-deoxy-6-thio-3'-(N',N'-dimethyl-amino-isobutyl)-α-D-glucofuranose;
1,2:3,5-Di-O-Isopropylidene-6-deoxy-6-thio-3'-(propan-1'-ol)-α-D-glucafuranose; and
1,2-O-Isopropylidene-6-deoxy-6-thio-3'-(phenylpropyl)-α-D-glucofuranose.

8. A pharmaceutical composition comprising a pharmaceutically effective amount of a compound according to claim 7 and a pharmaceutically acceptable carrier.

9. A method of treating an animal or human suffering from an inflammatory or autoimmune disorder or both comprising administering thereto an effective amount for treating the disorder of the compound according to claim 7.

10. A pharmaceutical composition comprising a pharmaceutically effective amount of a compound according to claim 1 and a pharmaceutically acceptable carrier.

11. A method of treating an animal or human suffering from an inflammatory or autoimmune disorder or both comprising administering thereto an effective amount for treating the disorder of the compound according to claim 1.

* * * * *

UNITED STATES PATENT AND TRADEMARK OFFICE
CERTIFICATE OF CORRECTION

PATENT NO. : 5,298,494
DATED : March 29, 1994
INVENTOR(S) : Sudershan K. Arora and Albert V. Thomas It is certified that error appears in the above-indentified patent and that said Letters Patent is hereby corrected as shown below:

On the Title Page, item [75], delete "Roy L. Whistler, West Lafayette, Indiana"

Column 44, line 30, "aD" should read -- a-D--.

Signed and Sealed this

Twelfth Day of July, 1994

Attest:

BRUCE LEHMAN

Attesting Officer

Commissioner of Patents and Trademarks